US012061670B2

(12) United States Patent
Novkov et al.

(10) Patent No.: US 12,061,670 B2
(45) Date of Patent: Aug. 13, 2024

(54) MACHINE-LEARNING IMAGE RECOGNITION FOR CLASSIFYING CONDITIONS BASED ON VENTILATORY DATA

(71) Applicant: Covidien LP, Mansfield, MA (US)

(72) Inventors: Donald J. Novkov, Encinitas, CA (US); Matthew J. Phillips, Carlsbad, CA (US)

(73) Assignee: Covidien LP, Mansfield, WA (US)

( * ) Notice: Subject to any disclaimer, the term of this patent is extended or adjusted under 35 U.S.C. 154(b) by 451 days.

(21) Appl. No.: 17/518,286

(22) Filed: Nov. 3, 2021

(65) Prior Publication Data

US 2022/0198219 A1 Jun. 23, 2022

Related U.S. Application Data

(60) Provisional application No. 63/127,892, filed on Dec. 18, 2020.

(51) Int. Cl.
*G06F 18/214* (2023.01)
*G06F 18/21* (2023.01)
*G06V 40/10* (2022.01)
*G16H 50/20* (2018.01)
*G06V 40/50* (2022.01)

(52) U.S. Cl.
CPC ........ *G06F 18/214* (2023.01); *G06F 18/2178* (2023.01); *G06V 40/10* (2022.01); *G16H 50/20* (2018.01); *G06V 40/15* (2022.01); *G06V 40/53* (2022.01)

(58) Field of Classification Search
CPC .............. A61M 16/101; A61M 16/107; A61M 16/201; G06H 10/63; G06H 20/40; G16H 50/20
See application file for complete search history.

(56) References Cited

U.S. PATENT DOCUMENTS 9,180,270 B2 * 11/2015 Kapust .............. A61M 16/0066
9,227,034 B2 * 1/2016 Kapust .............. A61M 16/0666
9,675,774 B2 * 6/2017 Cipollone ......... A61M 16/0057
(Continued)

FOREIGN PATENT DOCUMENTS

WO 2012/085741 A1 6/2012

OTHER PUBLICATIONS

International Search Report for International Application No. PCT/US2021/062294 mailed Apr. 5, 2022 (4 pages).
(Continued)

*Primary Examiner* — Yosef Kassa

(57) ABSTRACT

The technology relates to methods and systems for recognition of conditions from ventilation data. The methods may include acquiring ventilation data for ventilation of a patient during a time period; generating an image based on the acquired ventilation data; providing, as input into a trained machine learning model, the generated image, wherein the trained machine learning model was trained based on images having a same type as the generated image; and based on output from the trained machine learning model, generating a predicted condition of the patient. The image may be generated by storing ventilatory data as pixel channel values to generate a human-indecipherable image.

**20 Claims, 16 Drawing Sheets
(5 of 16 Drawing Sheet(s) Filed in Color)**

(56) References Cited

U.S. PATENT DOCUMENTS

| | | | |
|---|---|---|---|
| 10,682,288 B1 * | 6/2020 | Elia | G16H 40/63 |
| 10,709,864 B2 * | 7/2020 | Kapust | A61M 16/0493 |
| 10,872,811 B2 * | 12/2020 | Chen | H01L 23/5283 |

OTHER PUBLICATIONS

International Written Opinion for International Application No. PCT/US2021/062294 mailed Apr. 5, 2022 (12 pages).

Asanti et al. "Automatic Classification of Respiratory Sounds Considering Time Series Information Based on VGG16 with LSTM." 20th International Conf. on Control Automation and Systems, Oct. 13, 2022.

Raghu et al. "EEG based multi-class seizure type classification using convolutional neural network and transfer learning." Neural Networks, vol. 124, Jan. 25, 2020.

* cited by examiner

MACHINE-LEARNING IMAGE RECOGNITION FOR CLASSIFYING CONDITIONS BASED ON VENTILATORY DATA

CROSS-REFERENCE TO RELATED APPLICATIONS

This application claims the benefit of U.S. Provisional Application No. 63/127,892 filed Dec. 18, 2020, entitled "Machine-Learning Image Recognition for Classifying Conditions Based on Ventilatory Data," which is incorporated herein by reference in its entirety.

INTRODUCTION

Medical ventilator systems have long been used to provide ventilatory and supplemental oxygen support to patients. These ventilators typically comprise a connection for pressurized gas (air, oxygen) that is delivered to the patient through a conduit or tubing. As each patient may require a different ventilation strategy, modern ventilators may be customized for the particular needs of an individual patient. Determining the particular needs of the individual patient may be based on clinical conditions of the patient.

It is with respect to these and other general considerations that the aspects disclosed herein have been made. Also, although relatively specific problems may be discussed, it should be understood that the examples should not be limited to solving the specific problems identified in the background or elsewhere in this disclosure.

SUMMARY

The present technology relates to predicting clinical conditions of ventilation patients, such as patients, through the use of image-classifying machine-learning models. In an aspect, the technology relates to a computer-implemented method for recognition of conditions from ventilatory data. The method includes acquiring ventilatory data for ventilation of a patient during a time period; converting the ventilatory data to a human-indecipherable image having a plurality of pixels, wherein each of the pixels of the human-indecipherable image is defined by at least a first channel, and a first channel value of a first pixel represents at least a portion of a value for the ventilatory data; providing, as input into a trained machine learning model, the human-indecipherable image; and based on output from the trained machine learning model, generating a predicted condition of the patient.

In an example, the ventilatory data includes at least one of pressure data, flow data, or volume data. In another example, the first pixel is further defined by a second channel value and a third channel value. In a further example, the second channel value represents another portion of the value for the ventilatory data and the third channel value represents a sign for the ventilatory data. In still another example, the value for the ventilatory data represented by the first channel is a first value for ventilatory data at a first time point; the second channel value represents a second value for ventilatory data at a second time point; and the third channel value represents a third value for ventilatory data at a third time point. In yet another example, the first pixel is further defined a fourth channel value, and the fourth channel value represents a fourth value for ventilatory data a fourth time point. In still yet another example, the method further includes acquiring control parameters during the time period, wherein the control parameters are also converted into the human-indecipherable image.

In another example, the human-indecipherable image has a size of less than 4000 pixels. In a further example, the human-indecipherable image has a size of less than 1600 pixels. In yet another example, the ventilatory data includes pressure data sampled for at least 1000 time points and flow data sampled for at least 1000 time points. In still another example, the machine learning model is a convolutional neural network. In still yet another example, the method further includes displaying the predicted condition on a display of the ventilator. In another example, the predicted condition is at least one of asthma, acute respiratory distress syndrome (ARDS), emphysema, or chronic obstructive pulmonary disease (COPD).

In another aspect, the technology relates to a method for recognition of conditions from ventilatory data. The method includes acquiring ventilatory data and control parameters for ventilation of a patient during a time period; converting the ventilatory data to a human-decipherable image having a defined layout including plurality of layout sections, including a first section for a graphical representation of ventilatory data and a second section for a graphical representation of control parameters; providing, as input into a trained machine learning model, the human-decipherable image, wherein the trained machine learning model was trained based on images having the defined layout; and based on output from the trained machine learning model, generating a predicted condition of the patient.

In an example, the ventilatory data includes at least one of pressure data, flow data, or volume data. In another example, the first section includes a graphical representation of the pressure data in a first color and a graphical representation of flow in a second color. In yet another example, the graphical representation of the pressure data is a plot of pressure data versus time for the time period. In a further example, the graphical representation of control parameters are represented as bars, wherein a height of each bar represents a value for a control parameter. In still another example, the defined layout includes a third section for a scale of the ventilatory data.

In another example, the machine learning model is a neural network. In still another example, the graphical representation of the ventilatory data includes at least one of a scatter plot, a line graph, a spiral graph, a heat map, a polar area diagram, or a bar graph. In a further example, the human-decipherable image is generated in response to activation of a prediction mode of a ventilator.

In another aspect, the technology relates to a computer-implemented method for recognition of conditions from ventilatory data. The method includes acquiring ventilatory data for ventilation of a patient during a time period, wherein the ventilatory data includes at least pressure data and flow data; and converting the ventilatory data to a human-indecipherable image having a plurality of pixels. The plurality of pixels includes a first pixel having a first channel value representing at least a portion of a value of the pressure data at a first time point; and a second pixel having a first channel value representing at least a portion of a value of the flow data at the first time point. The method further includes providing, as input into a trained machine learning model, the human-indecipherable image; and based on output from the trained machine learning model, generating a predicted condition of the patient.

In an example, the plurality of pixels includes a third pixel having a first channel representing a value for a control parameter at the first time point. In another example, the first pixel includes a second channel value representing another portion of the value of the pressure data at the first time point. In a further example, the first pixel includes a third channel value representing a sign of the value of the pressure data at the first time point.

In another aspect, the technology relates to a computer-implemented method for recognition of conditions from ventilatory data. The method includes receiving ventilatory data comprising pressure or flow data of a ventilated patient; generating an image comprising pixels having pixel channels, wherein the ventilatory data is contained in the pixel channels; providing the generated image as input into a trained machine learning model, to produce an output; classifying a clinical condition of the patient based on the output; and adjusting a ventilatory setting or display according to the clinical condition of the patient.

In an example, the ventilatory data includes at least one of pressure data, flow data, or volume data. In a further example, the image is a human-indecipherable image. In still another example, the method further includes displaying the clinical condition of the patient with a prompt to confirm or reject the clinical condition. In yet another example, the method further includes receiving a response to the prompt; and based on the received response to the prompt, reinforcing the trained machine learning model.

In another aspect, the technology relates to a medical system that includes a medical ventilator; a processor; a trained machine-learning model; and memory storing instructions that when executed by the processor causes the system to perform a set of operations. The set of operations comprise receiving, from the ventilator, ventilatory data of a patient; generating an image comprising the ventilatory data stored in one or more pixel channels of pixels of the image; providing, as input into the trained machine learning model, the generated image; output, from the trained machine learning model, a predicted condition of the patient; and adjusting, on the ventilator, a ventilation setting or display based on the predicted condition.

In an example, the processor and the memory are housed within the ventilator. In another example, the system further includes a server in communication with the ventilator, wherein the processor and the memory are housed within the server. In a further example, the ventilatory data includes at least one of pressure data, flow data, or volume data.

In another aspect, the technology relates to a computer-implemented method for recognition of conditions from ventilation data. The method includes acquiring ventilation data for ventilation of a patient during a time period; generating an image based on the acquired ventilation data; providing, as input into a trained machine learning model, the generated image, wherein the trained machine learning model was trained based on images having a same type as the generated image; and based on output from the trained machine learning model, generating a predicted condition of the patient.

In an example, the ventilation data includes at least one of pressure data, flow data, or volume data. In another example, the image is a human-decipherable image. In still another example, the image is a human-indecipherable image.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter. It is to be understood that both the foregoing general description and the following Detailed Description are explanatory and are intended to provide further aspects and examples of the disclosure as claimed.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The following drawing figures, which form a part of this application, are illustrative of aspects of systems and methods described below and are not meant to limit the scope of the disclosure in any manner, which scope shall be based on the claims.

Figure 1:
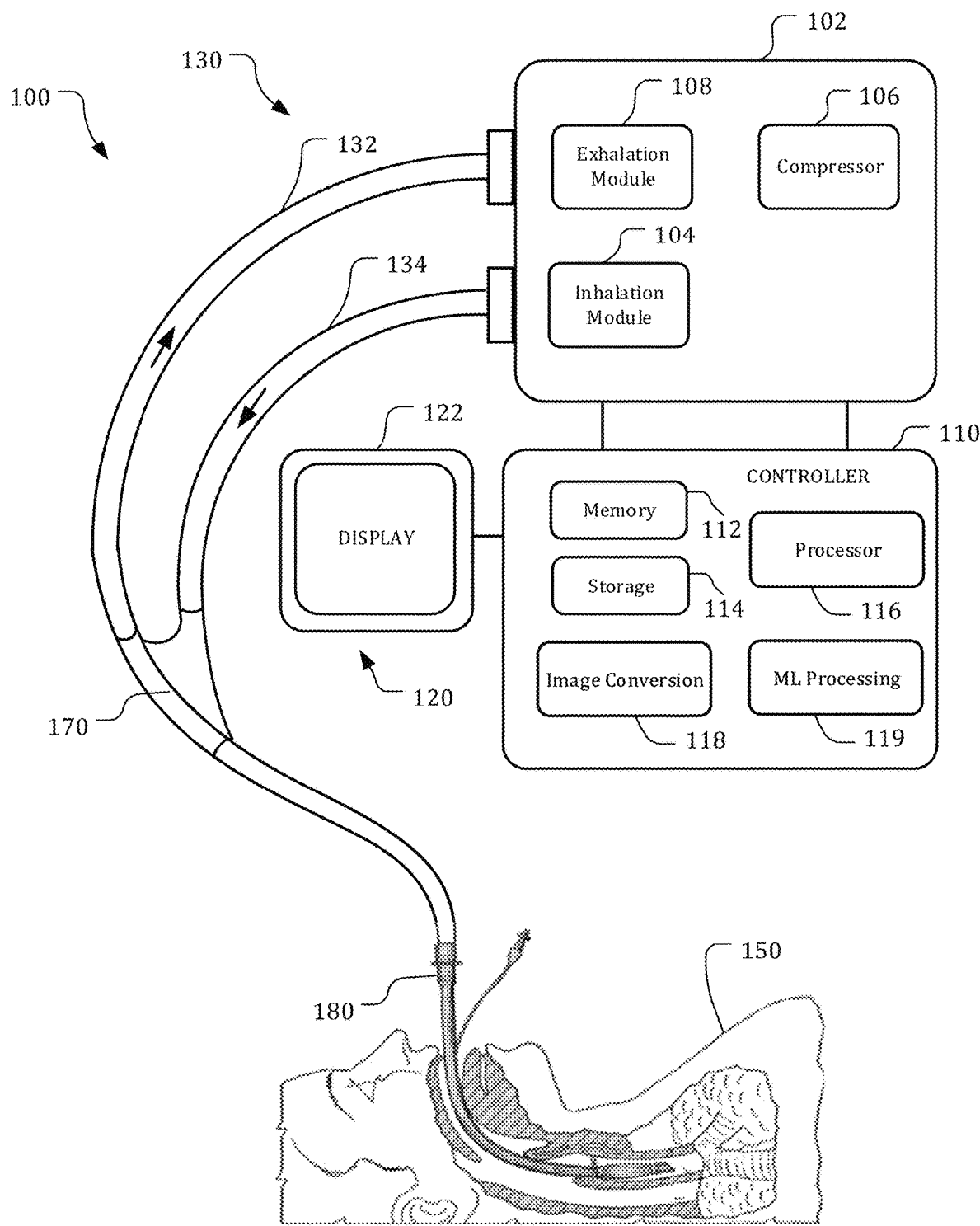
FIG. 1 is a diagram illustrating an example of a medical ventilator connected to a human patient.

While examples of the disclosure are amenable to various modifications specific aspects have been shown by way of example in the drawings and are described in detail below. The intention is not to limit the scope of the disclosure to the particular aspects described. On the contrary, the disclosure is intended to cover all modifications, equivalents, and alternatives falling within the scope of the disclosure and the appended claims.

DETAILED DESCRIPTION

As discussed briefly above, medical ventilators are used to provide breathing gases to patients who are otherwise unable to breathe sufficiently. The mode of ventilation and/or the settings for ventilation may be set based on the particular patient and any clinical conditions of the patient, such as asthma, acute respiratory distress syndrome (ARDS), emphysema, or chronic obstructive pulmonary disease (COPD), among others. By properly adjusting the ventilator settings based on the clinical condition of the patient, the ventilator can better support the patient, and the patient may be more likely to recover more quickly or be weaned from the ventilator more quickly. Identifying the clinical condition of the patient, however, is difficult and is often based on a physical examination of the patient by a physician or respiratory therapist. In some cases, internal imaging procedures, such as x-rays, have also been used by physicians to identify a clinical condition of the patient.

The present technology provides for methods and systems that can automatically predict a clinical condition of a patient based on ventilatory data of the patient, such as pressure data, flow data, and/or volume data measured or generated during ventilation of the patient. The present technology may also generate recommended settings for the ventilator based on the predicted clinical condition. The present technology is able to predict the clinical condition through the use of machine-learning, image-recognition technology. The systems and methods described herein generate images from the patient's ventilatory data. The images may be human-decipherable images that include plots of data versus time. The images may also include human-indecipherable images that include ventilatory data stored in the pixel channels themselves. For example, a pixel may have three channels (e.g., a red channel, a blue channel, and a green channel) that define its display properties. The ventilatory data may be stored directly in one or more channels of the pixels that form the human-indecipherable images. The generated images may then be provided to a trained machine-learning model, such as a neural network, that has been trained on a series of prior images corresponding to known clinical conditions. Thus, the trained machine-learning model is able to classify the newly received images for a particular patient and provide a prediction of the patient's clinical condition. By first converting the patient's ventilatory data to an image, the present technology is able to leverage image recognition and image classification techniques to identify a condition (a clinical condition of the patient) that is not based in an image of the patient, such as an x-ray of the patient.

FIG. 1 is a diagram illustrating an example of a medical ventilator 100 connected to a patient 150. The ventilator 100 may provide positive pressure ventilation to the patient 150. Ventilator 100 includes a pneumatic system 102 (also referred to as a pressure generating system 102) for circulating breathing gases to and from patient 150 via the ventilation tubing (also called a breathing circuit) 130. The ventilation tubing 130 couples the patient 150 to the pneumatic system via a patient interface 180. The patient interface 180 may be invasive (e.g., endotracheal tube, as shown) or non-invasive (e.g., nasal or oral mask, nasal cannula). The ventilator 100 controls the flow of gases into the ventilation tubing 130 by controlling (adjusting, opening, or closing) an inhalation flow valve or blower which may be part of the inhalation module 104. Additionally, a humidifier may be placed along the ventilation tubing 130 to humidify the breathing gases being delivered to the patient 150. A pressure sensor and flow sensor may be located at or near the inhalation module 104 and/or the exhalation module 108 to measure flow and pressure.

The ventilation tubing 130 may be a two-limb circuit (shown) or a one-limb circuit (also called single limb, with an inhalation side only). In a two-limb example, a wye-fitting 170, may be provided to couple the patient interface 180 to an inhalation limb 134 and an exhalation limb 132 of the ventilation tubing 130.

Pneumatic system 102 may have a variety of configurations. In the present example, system 102 includes an exhalation module 108 coupled with the exhalation limb 132 and an inhalation module 104 coupled with the inhalation limb 134. A compressor 106 or blower or other source(s) of pressurized gases (e.g., air, oxygen, and/or helium) is coupled with inhalation module 104 to provide breathing gas to the inhalation limb 134. The pneumatic system 102 may include a variety of other components, including mixing modules, valves, sensors, tubing, accumulators, filters, etc., which may be internal or external sensors to the ventilator (and may be communicatively coupled, or capable communicating, with the ventilator).

Controller 110 is operatively coupled with pneumatic system 102, signal measurement and acquisition systems, and a user interface 120. Controller 110 may include hardware memory 112, one or more processors 116, storage 114, and/or other components of the type found in command and control computing devices. In the depicted example, user interface 120 includes a display 122 that may be touch-sensitive and/or voice-activated, enabling the display 122 to serve both as an input and output device to enable a user to interact with the ventilator 100 (e.g., change ventilation settings, select operational modes, view monitored parameters, etc.).

The memory 112 includes non-transitory, computer-readable storage media that stores software that is executed by the processor 116 and which controls the operation of the ventilator 100. In an example, the memory 112 includes one or more solid-state storage devices such as flash memory chips. In an alternative example, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

The ventilator may also include one or more image conversion instructions 118. The one or more image conversion instructions 118 include instructions that cause the ventilator 100 to generate the images discussed below, such as human-decipherable images and human-indecipherable images. In addition, the ventilator may also include one or more machine-learning (ML) processing instructions 119. The ML processing instructions 119 may include instructions for processing the generated images with a trained ML model, such as a trained neural network. In some examples, the trained ML model may be stored on the ventilator, and the classification of new images and predictions of patient conditions may be performed at least partially or completely on the ventilator itself. In other examples, the ventilator may communicate with other computing devices (such as via a wired or wireless distributed network) that perform at least some of the operations described herein.

Figure 2:
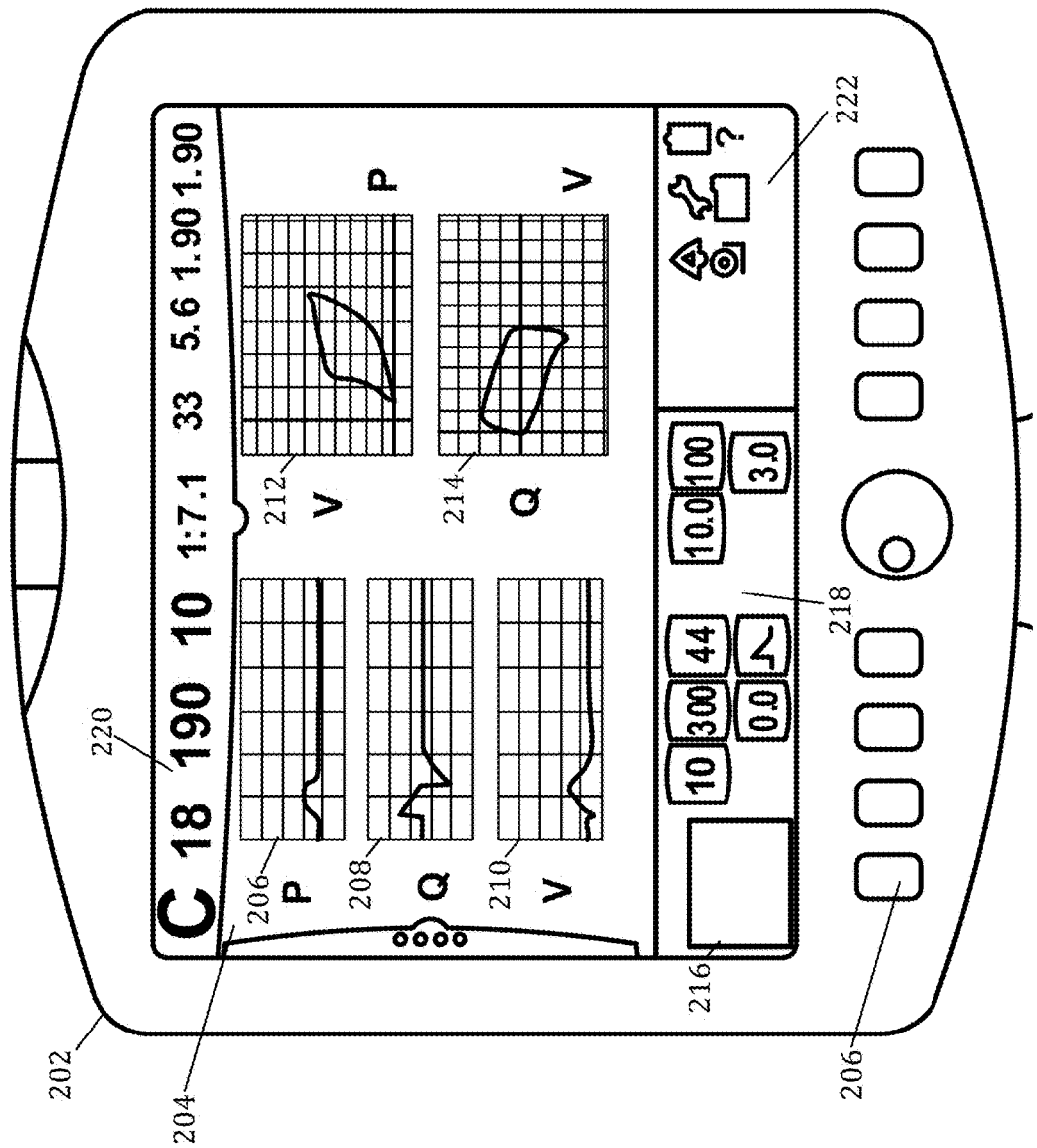
FIG. 2 is a is front view of an example display screen.

FIG. 2 is a front view of a display screen 202 coupled to a ventilator, according to an embodiment. Display screen 202 may be mounted to the ventilator or a separate screen, tablet, or computer that communicates with the ventilator. The display screen 202 presents useful information to the user and receives user inputs. The display presents a user interface 204, which include a graphical user interface (GUI) 204. The GUI 204 may be an interactive display, e.g., a touch-sensitive screen or otherwise, and may provide various windows (i.e., visual areas) comprising elements for receiving user input and interface command operations and for displaying ventilatory information (e.g., ventilatory data such as pressure, volume, and flow waveforms, inspiratory time, PEEP, baseline levels, etc.), and control information (e.g., alerts, patient information, control parameters, modes, etc.). The elements may include controls, graphics, charts, tool bars, input fields, icons, etc. The display screen 202 may also include physical buttons or input elements, such as dials, wheels, switches, buttons, etc.

In the interface 204 depicted in FIG. 2, a plurality of plots are displayed on the interface 204, including a pressure-time plot 206, a flow-time plot 208, a volume-time plot 210, a volume-pressure loop 212, a flow-pressure loop 214. The pressure-time plot 206 plots a measured or determined pressure versus time. The pressure may be measured from a pressure sensor in the ventilator or within the ventilation circuit. Pressure values may include inspiratory pressure, wye pressure, and/or expiratory pressure, among other pressure types. The flow-time plot 208 plots a measured or determined flow versus time. The flow may be measured from a flow sensor in the ventilator or within the ventilation circuit. Flow values include inspiratory flow, expiratory flow, and/or net flow, among other flow types. The volume-time plot 210 plots a determined volume versus time. The volume may be determined or calculated based on measured flow values. The volume-pressure loop 212 is of pressure versus volume during inspiration and expiration of the patient. The flow-volume loop is a plot of inspiratory and expiratory flow (on the y-axis) versus volume (on the x-axis).

The interface 204 may also include additional representations of data regarding the patient, ventilation settings, and/or control parameters. For example, a patient data segment 216 may include information about or based on the patient, such as whether the patient is a neonate, pediatric, or adult patient. The patient data may also include whether the mass or predicted body weight (PBW) of the patient, absolute tidal volume limits based on PBW, among other types of data. The patient data may be considered a control parameter in some examples as the type of patient and the PBW of the patient may be utilized in setting pressure, flow, and volume settings.

The interface may also include a first display section 218 and a second display section 220 for displaying various indicators of control parameters or other ventilation parameters. For instance, numerical values for parameters, such as compliance, resistance, end expiratory flow, end inspiratory pressure, total circuit pressure, exhaled mandatory tidal volume, exhaled minute volume, exhaled spontaneous minute volume, exhaled spontaneous tidal volume, exhaled tidal volume, expiratory sensitivity, expiratory time, apnea interval, expiratory time, total inspiratory and expiratory flow, flow sensitivity, flow triggering, inspiratory time to expiratory time ratio (I:E), inspiratory pressure, inspired tidal volume, positive end expiratory pressure (PEEP), mean circuit pressure, oxygen percentage, percent support setting, peak pressure, peak flow, peak, plateau pressure, plateau time, compensation pressure, pressure support level, pressure triggering, inspired tidal volume, exhaled tidal volume, rise time percent, vital capacity, and volume support settings, among others.

The interface may also include a settings panel 222 with various icons that may be selected to enter different settings for the ventilator. For example, ventilation settings and/or control parameters may be entered, e.g., by a clinician based on a prescribed treatment protocol for the particular patient, or automatically generated by the ventilator, e.g., based on known attributes of the patient (e.g., age, diagnosis, ideal body weight, predicted body weight, gender, ethnicity, etc.) or based on the predicted clinical condition of the patient. Ventilation settings and/or control parameters may include a plurality of different settings or parameters such as respiratory rate (f), tidal volume (VT), PEEP level, etc.

Figure 3A:
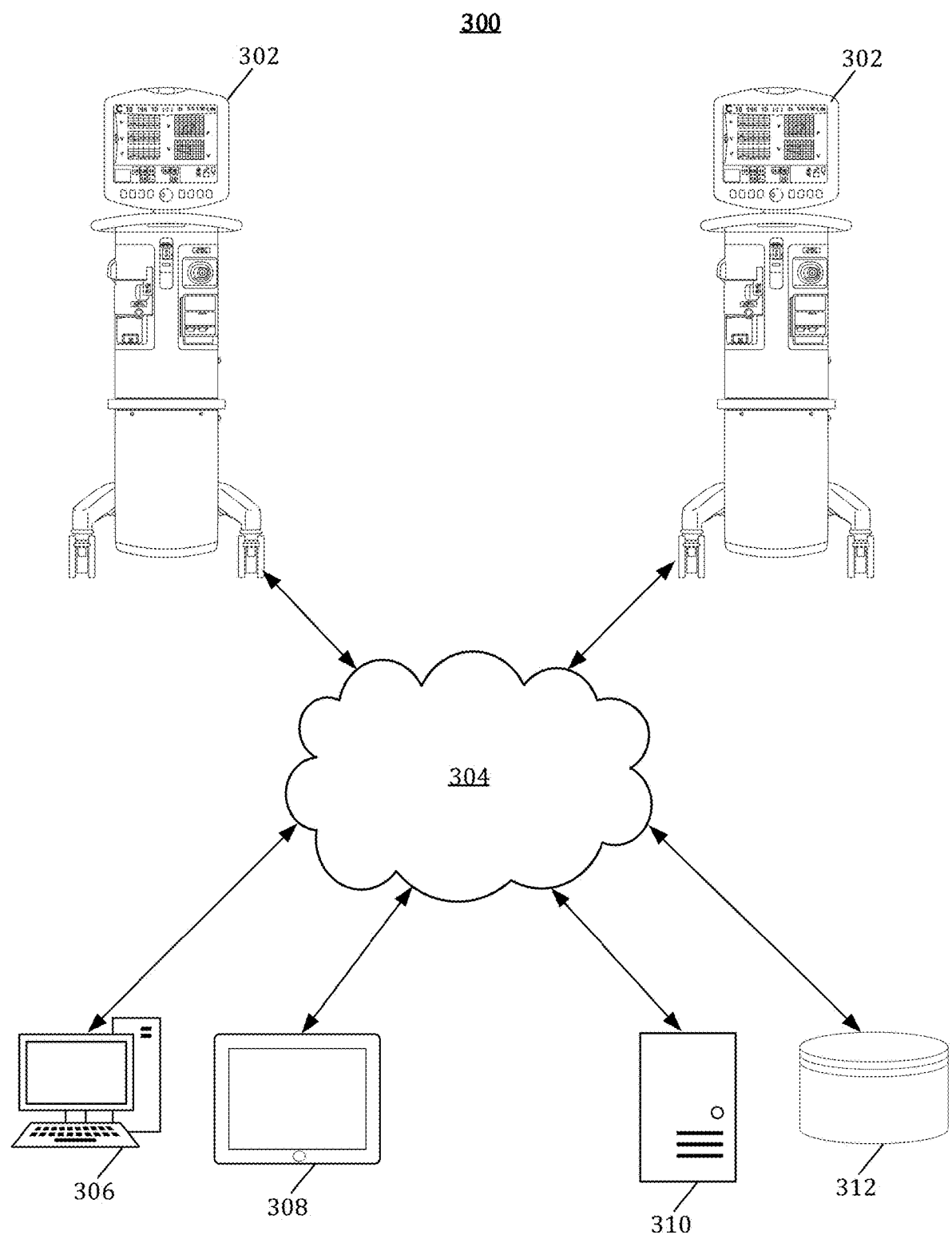
FIG. 3A depicts an example image-processing and condition-prediction system.

FIG. 3A depicts an example image-processing and condition-prediction system 300. The system 300 includes a distributed network 304 with one or more ventilators 302 and local or remote computing devices. Each of the ventilators 302 may include the features described above. In the example system 300, the ventilators 302 are in communication with other computing devices through the distributed network 304. The network 304 may include a plurality of servers or computing devices/components that are local or remote and connected via wired or wireless communications. For instance, additional computers 306, smart devices such as tablets 308, servers 310, and/or databases 312 may be in communication with the ventilator(s) 302 via the network 304.

The devices of the system 300 may receive ventilatory data and control parameters from the ventilators 302 and then perform one or more of the operations described herein. For example, one or more devices in the system 300 may convert the received ventilatory data and control parameters into the images discussed herein, such as the human-decipherable images and/or the human-indecipherable images. The devices in the system 300 may also perform the ML processing operations described herein. For instance, the devices may process the generated images in order to classify the images and provide a prediction of clinical condition of the patient for which the ventilatory data was generated. The predicted clinical condition may then be transmitted from one or more of the devices to the ventilator 302 from which the ventilatory data was received so that the ventilator 302 may display the predicted clinical condition. As an example, one of the servers 310 may be a training a server that trains the ML model. The training server may periodically retrain the ML model using additional training data, and the training server may then deploy the retrained or updated ML model. The same or another server 310 may be a deployment server that processes ventilatory data from a ventilated patient with the trained ML model to predict a clinical condition.

Figure 3B:
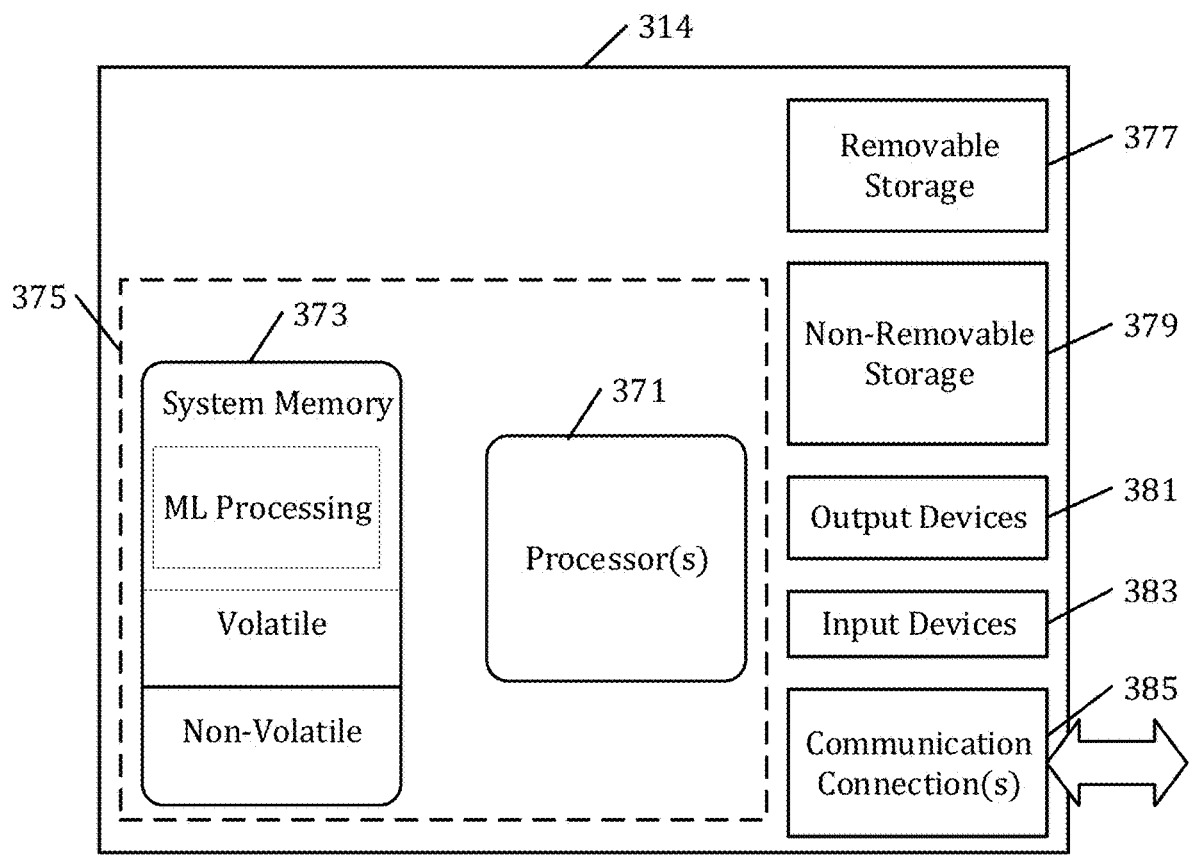
FIG. 3B depicts a schematic diagram illustrating features of the server.

FIG. 3B depicts a schematic diagram illustrating features of an example device of system 300, such as computer 306, tablet 308, server 310, and/or database 312. In its most basic configuration, device 314 typically includes at least one processor 371 and memory 373. Depending on the exact configuration and type of computing device, memory 373 (storing, among other things, instructions to perform the image generation and ML processing operations disclosed herein) can be volatile (such as RAM), non-volatile (such as ROM, flash memory, etc.), or some combination of the two. The processors 371 may include central processing units (CPUs) and/or graphical processing units (GPUs), among other potential types of processors. In some examples, the ML model calculations may be performed by one or more GPUs. This most basic configuration is illustrated in FIG. 3B is indicated by dashed line 375. Further, device 314 may also include storage devices (removable, 377, and/or non-removable, 379) including, but not limited to, solid-state devices, magnetic or optical disks, or tape. Similarly, device 314 may also have input device(s) 383 such as a touch screen, keyboard, mouse, pen, voice input, etc., and/or output device(s) 381 such as a display, speakers, printer, etc. Also included in the environment can be one or more communication connections 385, such as LAN, WAN, point to point, Bluetooth, RF, etc.

Device 314 typically includes at least some form of computer readable media. Computer readable media can be any available media that can be accessed by processor 371 or other components within device 314. By way of example, and not limitation, computer readable media can comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible and non-transitory medium which can be used to store the desired information.

Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

According to embodiments described below, a system is provided for predicting clinical conditions of a patient, ventilator, or interaction between the patient and the ventilator based on a machine-learning model that utilizes images of ventilator data. The system accepts current ventilatory data from a ventilated patient (such as pressure, flow, volume, and other data), converts the data into an image format, and then passes the image(s) into a trained ML model that classifies clinical conditions from the image data. By presenting and analyzing the ventilator data in image formats, the system is able to benefit from image processing and training techniques. Additionally, the patient data (vital signs, ventilatory data, and other data as described below) can be handled in a way that maintains privacy, by formatting this data in format that is not human-readable.

Figure 4A:
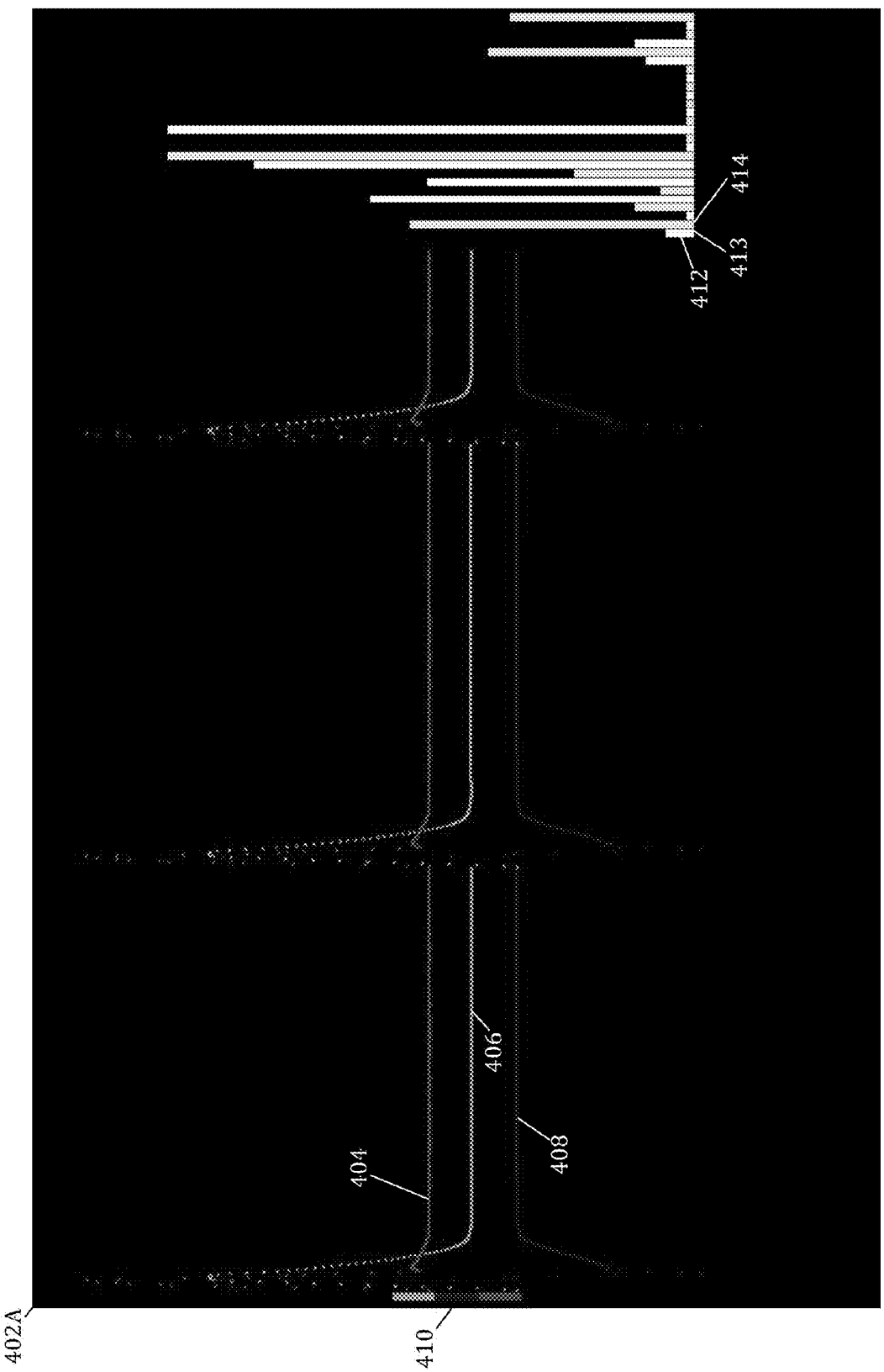
FIGS. 4A-4D depict examples of a human-decipherable images.
Figure 4B:
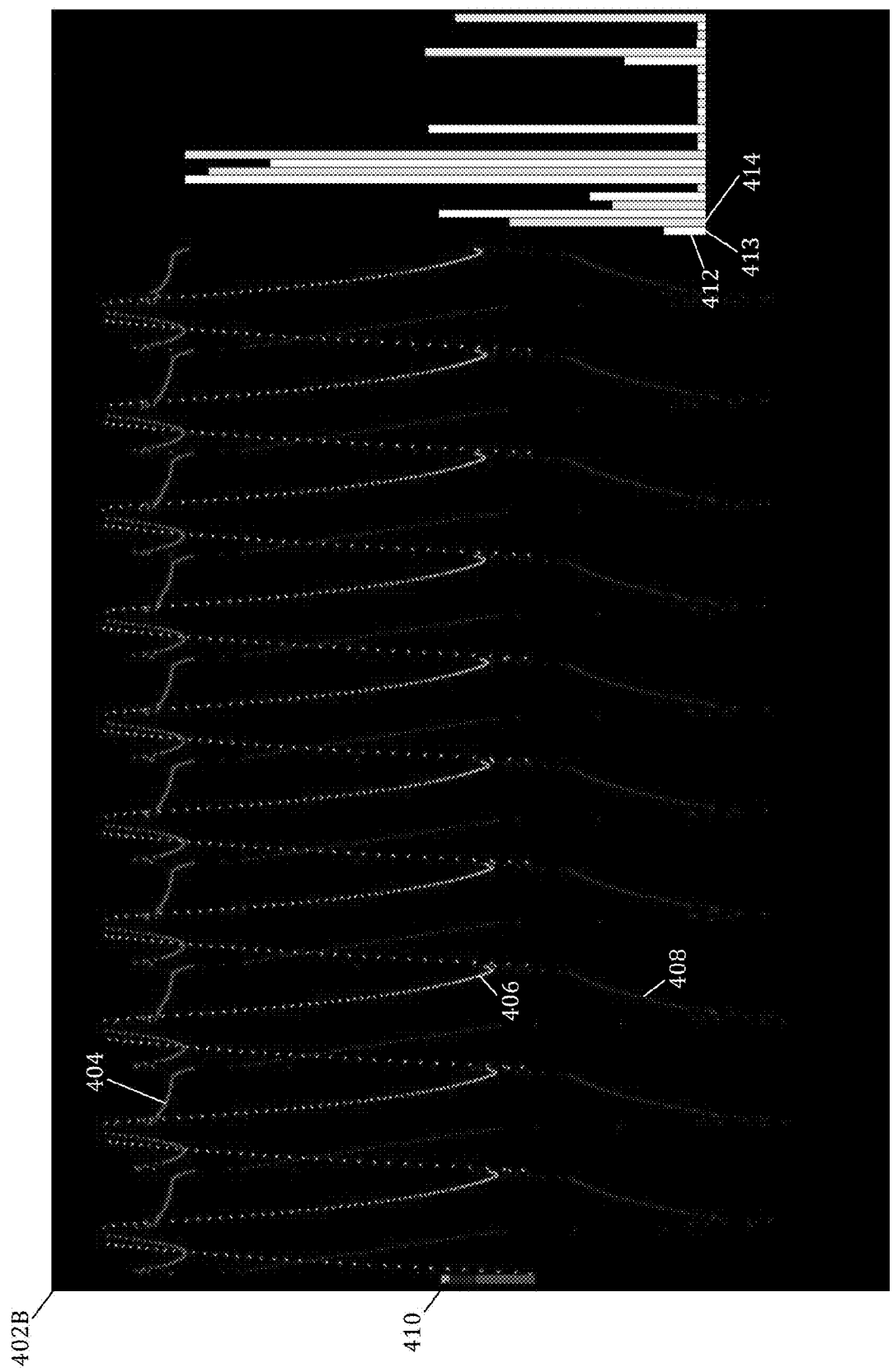
Figure 4C:
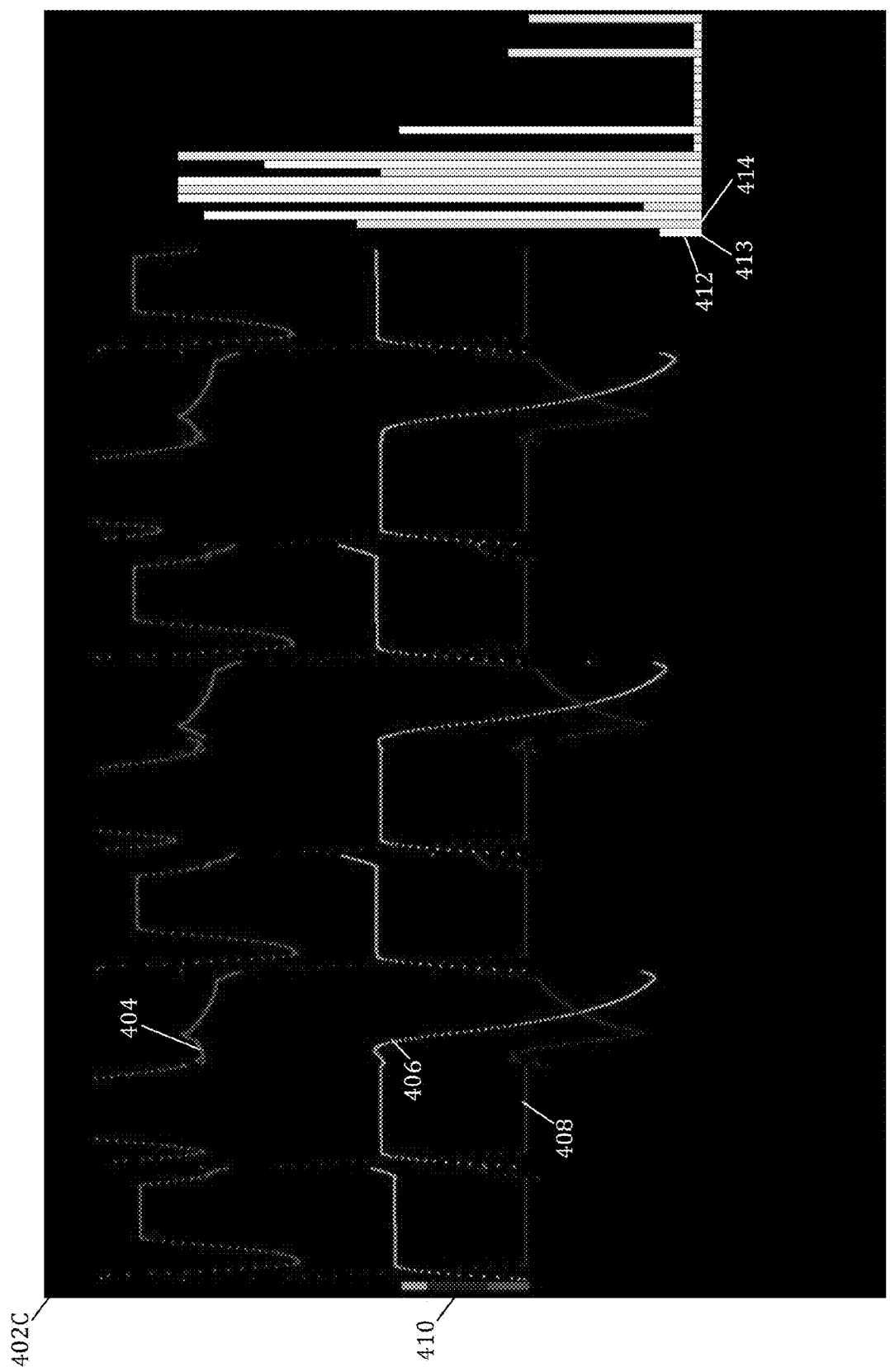

FIGS. 4A-4C depict examples of ventilatory data presented in the form of human-decipherable images 402A-C. The human-decipherable images 402A-C are generated based on ventilatory data that is acquired during ventilation of a patient. In the examples depicted, the ventilatory data includes pressure data, flow data, and volume data. This data may be measured directly from sensors within the ventilator and tubing, or data may be derived or calculated from various measurements. Each image includes ventilatory data acquired over a time period. In the examples depicted, the time period is 24 seconds. In other examples, the time period may be more or less than 24 seconds. For instance, the time period may be less than one minute, less than 30 seconds, or less than 10 seconds. Different images or sets of images may be created from data over different time periods, and then used to identify different types of clinical conditions. The time period may be based on the type of clinical condition or conditions that are being predicted. For instance, some clinical conditions may be classified based on ventilatory data for a single breath or a portion of a breath (such as an inhalation phase or exhalation phase of a single breath, which may span a few seconds, such as 2-10 seconds). Other clinical conditions may require ventilatory data for multiple breaths (spanning more seconds or minutes, such as 10 seconds up to 2 minutes, 10 minutes, 30 minutes or longer) to be properly or accurately classified.

In each of the example human-decipherable images 402A-C, the patient's ventilatory data is displayed in human-decipherable graphical representations. A graphical representation of pressure data 404 is represented in a first color (red in the examples depicted). A graphical representation of volume data 406 is represented in a second color (green in the examples depicted). A graphical representation of flow data 408 is represented in a third color (blue in the examples depicted).

In the example human-decipherable images 402A-C, the pressure graphical representation 404, the volume graphical representation 406, and the flow graphical representation 408 are all provided as plots against time. For example, the pressure graphical representation 404 is provided as a plot of pressure data versus time for the time period for which the ventilatory data was captured. In image 402A in FIG. 4A, three distinct breaths can be seen corresponding to the peaks of the pressure data. Image 402B in FIG. 4B depicts an additional number of breaths (which correspond to the peaks of the pressure signal) within the same time frame, which indicates a higher frequency of breaths. Image 402B depicts yet a different number of breaths and on a different scale from the images 402A-B. The control parameters for ventilation of the patient from which images 402A-B were generated were also different for each of the images 402A-B.

As discussed above, in this example, the time period for which the ventilatory data was captured was 24 seconds. During that time period (e.g., those 24 seconds), the ventilatory data was captured or recorded every 20 milliseconds (ms) (other sampling rates are also possible). Accordingly, there are 1200 time points and thus 1200 data points for each type of ventilatory data (e.g., pressure, flow, and volume) in the examples depicted. Each pressure data point is represented by a single red pixel in the image, or multiple pressure data points are averaged together and presented as a single red pixel. For instance, the left-most red pixel may be for pressure at a first time point in the time period. Similarly, volume data is presented by a green pixel, and flow data by a blue pixel. These data points are plotted versus time in the image. The black areas of the human-decipherable images 402A-C are pixels that do not represent any type of ventilator data. Thus, the values for all three channels for the pixels at those positions are set to zero—thus providing their black appearance.

While the pressure graphical representation 404, the volume graphical representation 406, and the flow graphical representation 408 are plotted as scatter plots versus time, other data visualizations are also possible. For instance, the ventilatory data may also be presented as line graph, a spiral graph, a heat map, a polar area diagram, a bar graph, or other similar data visualization types. Further, as used herein, a "graphical representation" is a non-textual representation of the data. In addition, different types of data plots may be presented as well. For instance, data loops, such as volume-pressure loops or a flow-pressure loops, may be provided as part of the human-readable images 402A-C.

The colors used to represent each of the graphical representations 404-408 may be chosen based on the colors being primary colors in a color scheme used for the pixels of the image. For instance, in the example human-decipherable images 402A-C, a red-green-blue (RGB) color scheme is utilized for the image. Accordingly, each pixel of the human-decipherable images 402A-C may be defined by three channels—a red channel, a green channel, and a blue channel. Because the graphical representations 404-408 are each represented by a different primary color of the color scheme, for time points when the representations overlap, the data point for each graphical representation 404-408 may be determined based on an inspection of the channels for the pixel where the overlap occurs. Color schemes other than RGB (e.g., Cyan Magenta Yellow Black (CMYK); hue, saturation, lightness (HSL), etc.) may also be utilized, and the respective channels may then be used in similar manner, although the channels may correspond to a different displayed color.

The human-decipherable images 402A-C may also include a scale indicator 410. The scale indicator 410 represents the relative scale for each of the graphical representations of ventilatory data provided in the human-decipherable image. The scale indicator 410 includes a segment for each type of ventilatory data for which a graphical representation is provided in a human-decipherable image. In the depicted example, the scale indicator 410 includes three segments. The three segments include a first segment corresponding to the pressure graphical representation 404, a second segment corresponding to the volume graphical representation 406, and a third segment corresponding to the flow graphical representation 408. Each segment of the scale indicator 410 has a color that corresponds to the corresponding graphical representation of ventilatory data. In the examples depicted, the first segment has a red color because the pressure graphical representation 404 is represented as red pixels, the second segment has a green color because the volume graphical representation 406 is represented as green pixels, and the third segment has a blue color because the flow graphical representation 408 is represented as blue pixels. The height of each segment (e.g., the number of pixels of each segment) represents a relative scale for each of the graphical representations of data. The segments of the scale indicator may be generated based on the range of values for the ventilatory data. Each scale segment may be based on the maximum and minimum values for the corresponding ventilatory data. For example, the height of the red segment may be based on a maximum and a minimum of the pressure data in the pressure graphical representation 404.

The human-decipherable images 402A-C also include a control-parameters graphical representation 412 of the control parameters. The control parameters include parameters such as a respiratory rate setting (e.g., in beaths per minute), a maximum flow setting (e.g., in liters per minute (L/m)), a flow sensitivity setting (e.g., in L/m), a tidal volume setting (e.g., in liters), a PEEP setting (e.g., in $cmH_2O$ O), an oxygen percentage setting (ranging between 21% and 100%), a plateau setting (e.g., in seconds), a flow pattern setting (e.g., wave or ramp), ventilation mode (e.g., Assist-Control (A/C), Spontaneous (SPONT), Synchronized Intermittent Mandatory Ventilation (SIMV), BiLevel, CPAP, etc.), a mandatory mode type (e.g., Pressure Control (PC), Volume Control (VC)), a spontaneous mode type (e.g., Pressure Support (PS), Tube Compensation (TC), Volume Support (VS), Proportional Assist (PA)), an expiration sensitivity setting (e.g., in percentage or L/min), a support pressure setting (e.g., in $cmH_2O$), a predicted body weight (e.g, in kilograms), a PCV inspiratory pressure setting (e.g., in $cmH_2O$), a PCV inspiratory time setting (e.g., in seconds), an inspiratory component of an inspiratory-to-expiratory time (I:E) ratio, an I:E ratio, an expiratory time component of the I:E ratio, a rise time percentage setting, a PAV+ percent support setting, a monitored exhaled tidal volume (e.g., in liters), a monitored peak airway pressure (e.g., in $cmH_2O$), a monitored spontaneous percent inspiratory time, a monitored end expiratory flow, (e.g., in L/min), among other types of settings and parameters. In the examples depicted, control-parameters graphical representation 412 is presented as a bar chart. Each bar of the bar chart represents a different control parameter, and the height of each bar (e.g., the number of pixels in the bar) represents the value for the respective control parameter. A higher bar means a higher value for the particular control parameter. As an example, a first bar 413 may represent the inspiratory rate and the second bar 414 may represent a maximum flow setting. The bar chart may alternate in color to help visually distinguish between the different control parameters (e.g., distinguish the different bars from one another). While the control-parameters graphical representation 412 is presented as a bar graph, other data visualization types are also possible, such as pie charts, scatter plots, line graphs, etc.

In an embodiment, the data in the human-decipherable images 402A-C is arranged in a defined layout. The defined layout includes a plurality of sections or areas where the graphical representations are displayed. For instance, in the human-decipherable images 402A-C, the scale indicator 410 is located in the same position on the left side of each image. Similarly, ventilatory data graphical representations 404-408 are displayed across the same middle section of each of the human-decipherable images 402A-C. The control-parameters graphical representation 412 is displayed in the same bar chart section on the right side of each of the human-decipherable images 402A-C. By using a dedicated format for the type of data in each part of the image, a machine-learning model may be trained to classify the images according to clinical conditions, as discussed further herein. In addition, by using a defined layout, the images can be platform or ventilator-agnostic. For instance, the images may be generated from ventilatory data generated from any type of ventilator.

Figure 4D:
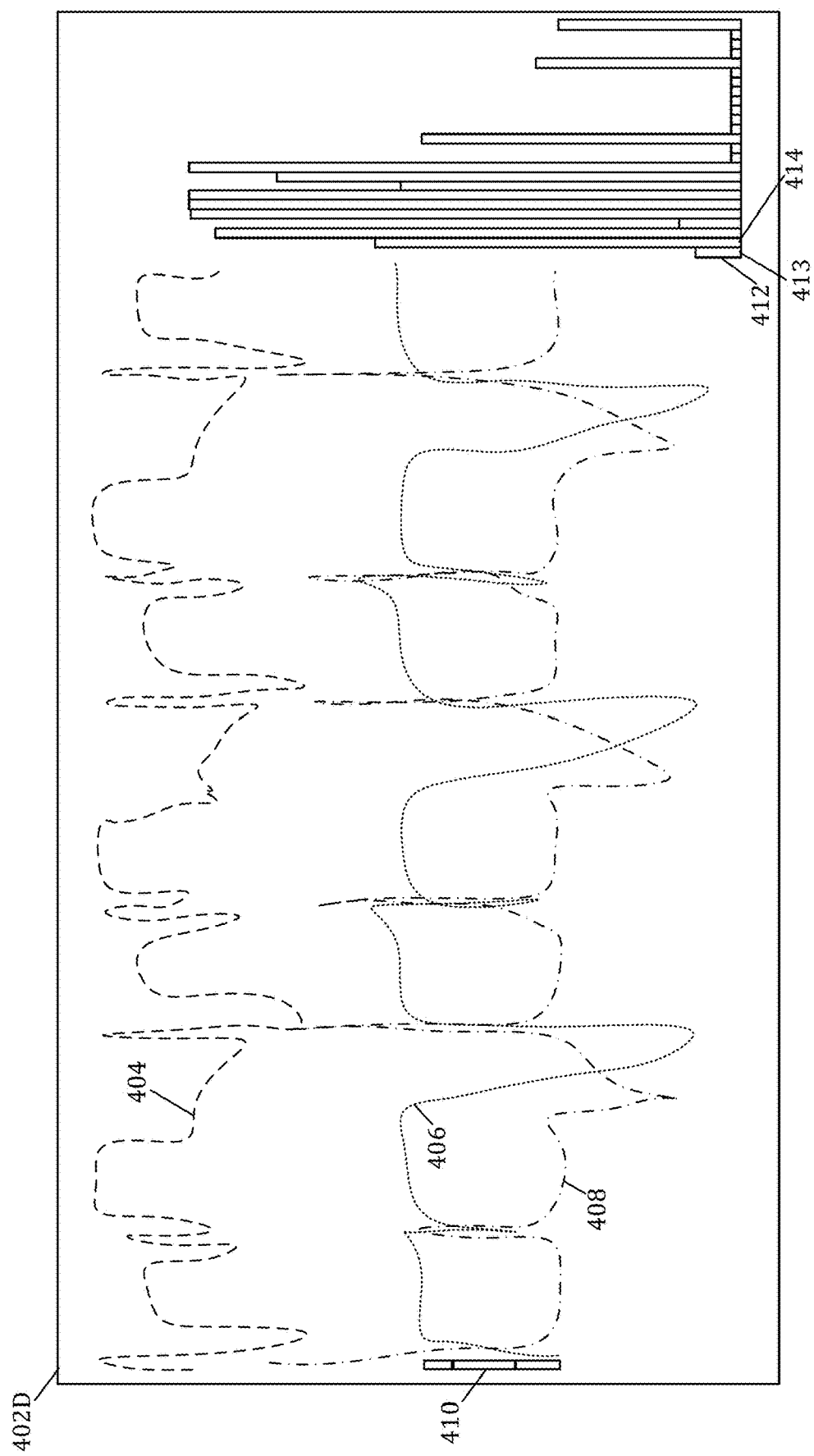

FIG. 4D is a copy of FIG. 4C in which the colors are shown in black and white, just for clarity. Pressure data 404 is shown in a dashed line which represents a red color (or other assigned color channel), volume data 406 is show in a dotted line which represents a green color (or other assigned color channel), and flow data 408 is shown in dash-dotted line which represents a blue color (or other assigned color channel).

Figure 4E:
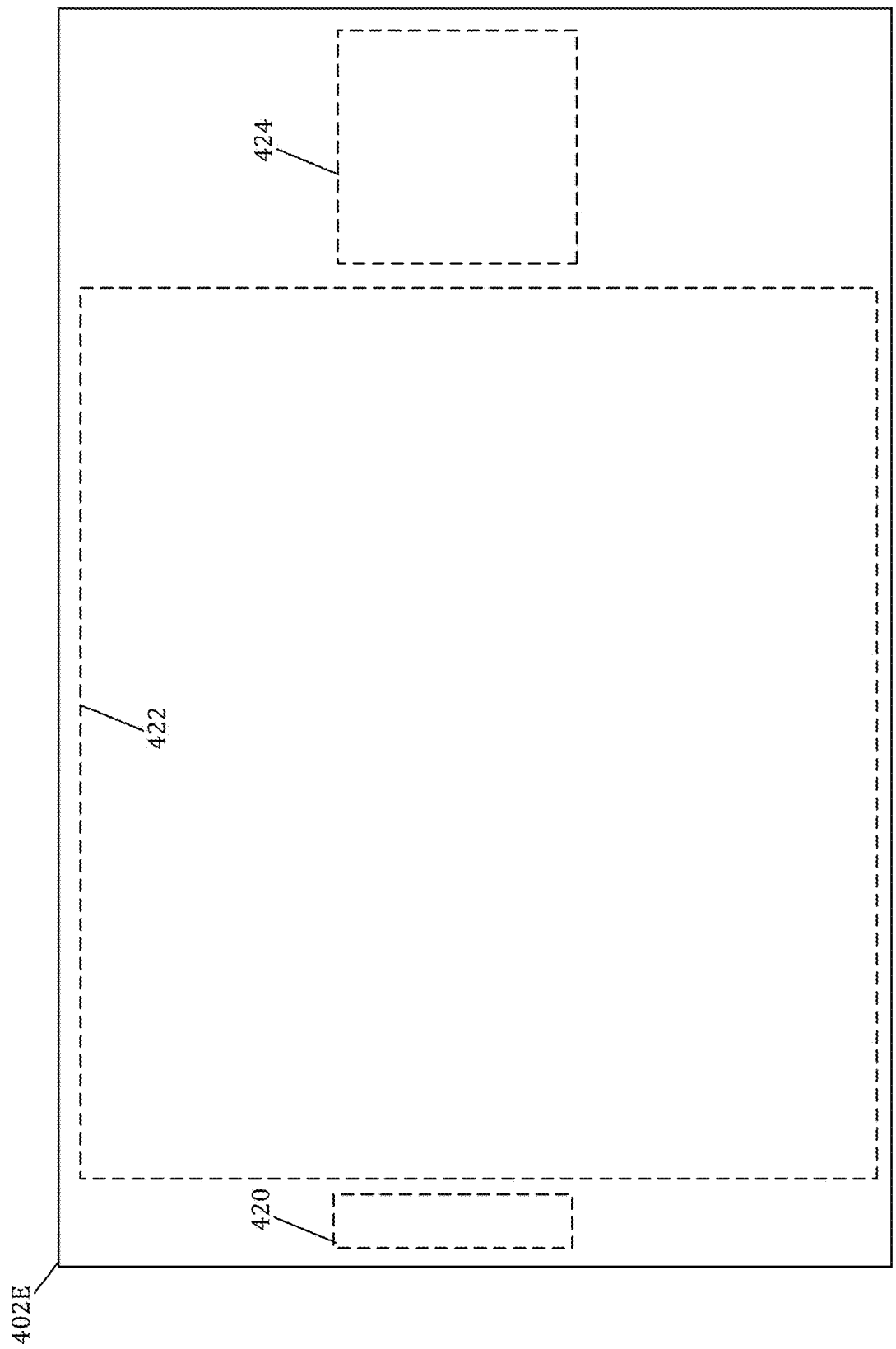
FIG. 4E depicts an example defined layout of a human-decipherable image.

FIG. 4E provides an example layout 402E of a human-decipherable image. The layout 402F includes a plurality of sections, including a scale section 420, a ventilatory data section 422, and a control parameters section 424. For each of the human-decipherable images 402A-C that is generated according the example defined layout, the scale indicator 410 is displayed in the scale section 420, the ventilatory data graphical representations 404-408 are displayed in the ventilatory data section 422, and the control-parameters graphical representation 412 is displayed in the control parameters section 424. By organizing the data in a consistent layout, an ML model can be trained to classify images that are provided to it in the same layout.

The size of each of the sections may be based on the amount of data that is to be represented in the human-decipherable image. For instance, the width of the ventilatory data section 422 may be based on the time period for which data was acquired and the sampling frequency for the time period. In the examples discussed above, the time period is every 24 seconds and the sampling frequency is every 20 ms, resulting in 1200 time points in the dataset. Thus, to represent the 1200 time points as ventilatory data versus time in a scatter plot, the ventilatory data section 422 needs to be at least 1200 pixels wide. Fewer pixels may be used if the data is averaged or sampled at a different frequency. Similarly, the width of the control parameters section 424 may be based on the number of different control parameters that are to be included in the control-parameters graphical representation 412. When using a bar chart format such as the format utilized in example human-decipherable images 402A-C above, one column of pixels is utilized for each different control parameter. Accordingly, the width of the control parameters section 424 may be at least as many pixels as there are different control parameters.

Figure 4F:
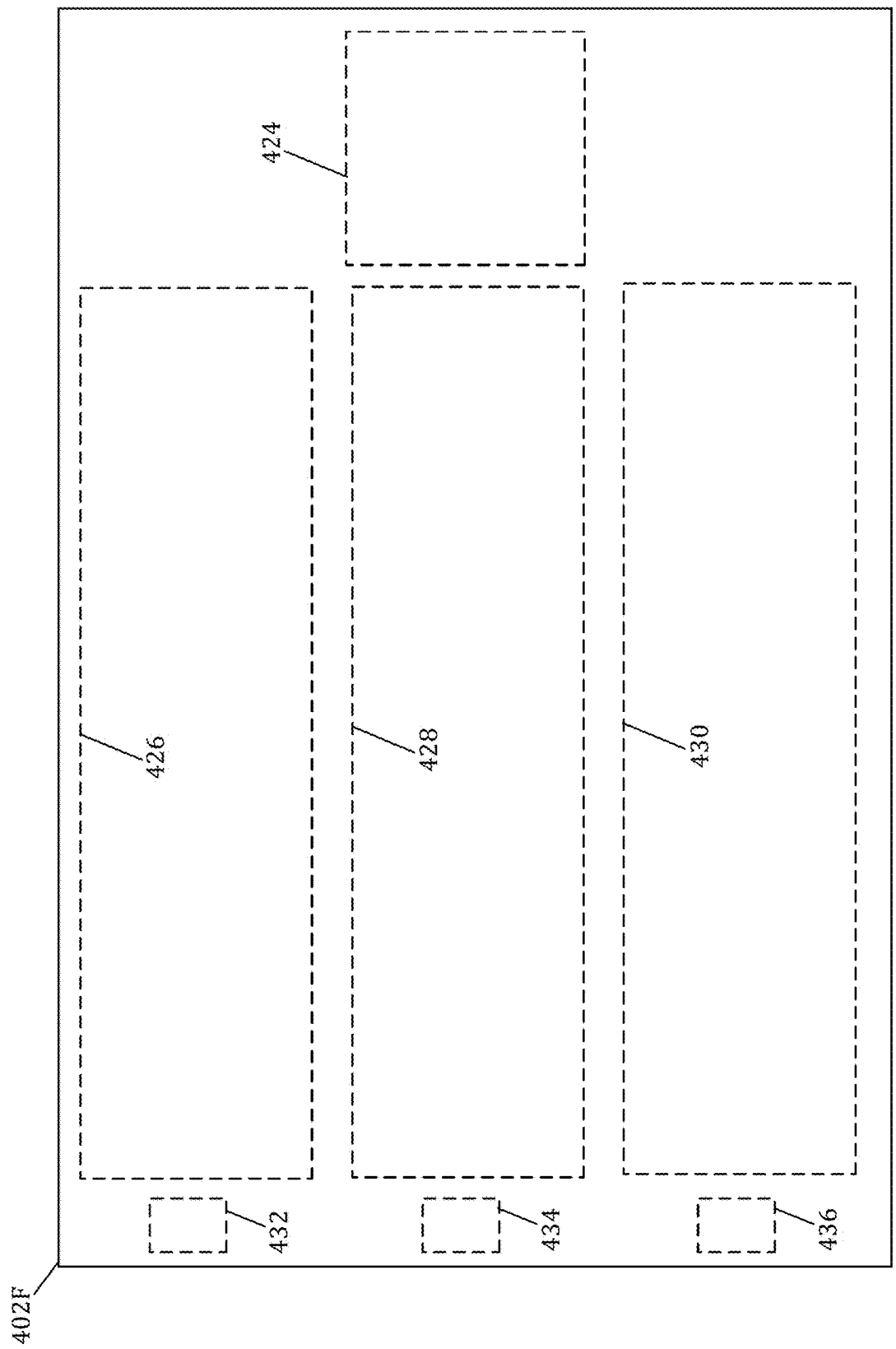
FIG. 4F depicts another example defined layout of a human-decipherable image.

FIG. 4F depicts another example layout 402F of a human-decipherable image. Similar to the layout 402E depicted in FIG. 4E, the layout 402F includes a plurality of sections. Rather than a single ventilatory data section, however, the layout 402F has multiple sections for displaying ventilatory data. In the example shown, the layout 402F includes a first ventilatory data section 426, a second ventilatory data section 428, and a third ventilatory data section 430. Each of the ventilatory data sections 426-430 may be for display of a certain type of ventilatory data. For instance, the first ventilatory data section 426 may be for display of pressure data, the second ventilatory data section 428 may be for display of volume data, and the third ventilatory data section 430 may be for display of flow data. Each of the ventilatory data sections 426-430 also may have a corresponding scale indicator section 432-436. For example, a first scale indicator section 432 is for display of a scale indicator corresponding to the ventilatory data displayed in the first ventilatory data section 426. By utilizing a layout such as layout 402F with separate ventilatory data sections 426-430, the different types ventilatory data (e.g., pressure, volume, flow) may not be displayed as separate colors because different types of ventilatory data will not overlap one another in the resultant image.

The images discussed above have been referred to herein as "human-decipherable" images because a human can generally identify the trends and relative values of the depicted graphical representations. For instance, the pressure, volume, and flow data are displayed as scatter plots of data versus time, which can be interpreted or understood by a human. For instance, a human can recognize the shapes and patterns, such as when pressure is increasing or decreasing. Human-decipherable images may include, for example, scatter plots, bar charts, pie charts, line charts, grids, and/or text. The present technology, however, may also utilize human-indecipherable images. The human-indecipherable images do not include graphical representations that can be deciphered by a human. Rather, the ventilatory data and the control parameters are incorporated as values in the channels of the pixels themselves, as discussed further below. The human-indecipherable images provide additional advantages such as storing and transmitting data in a manner that can maintain patient privacy. For instance, because the human-indecipherable images are not decipherable by viewing the image, additional privacy is created by storing the ventilatory data in such a format.

Figure 5A:
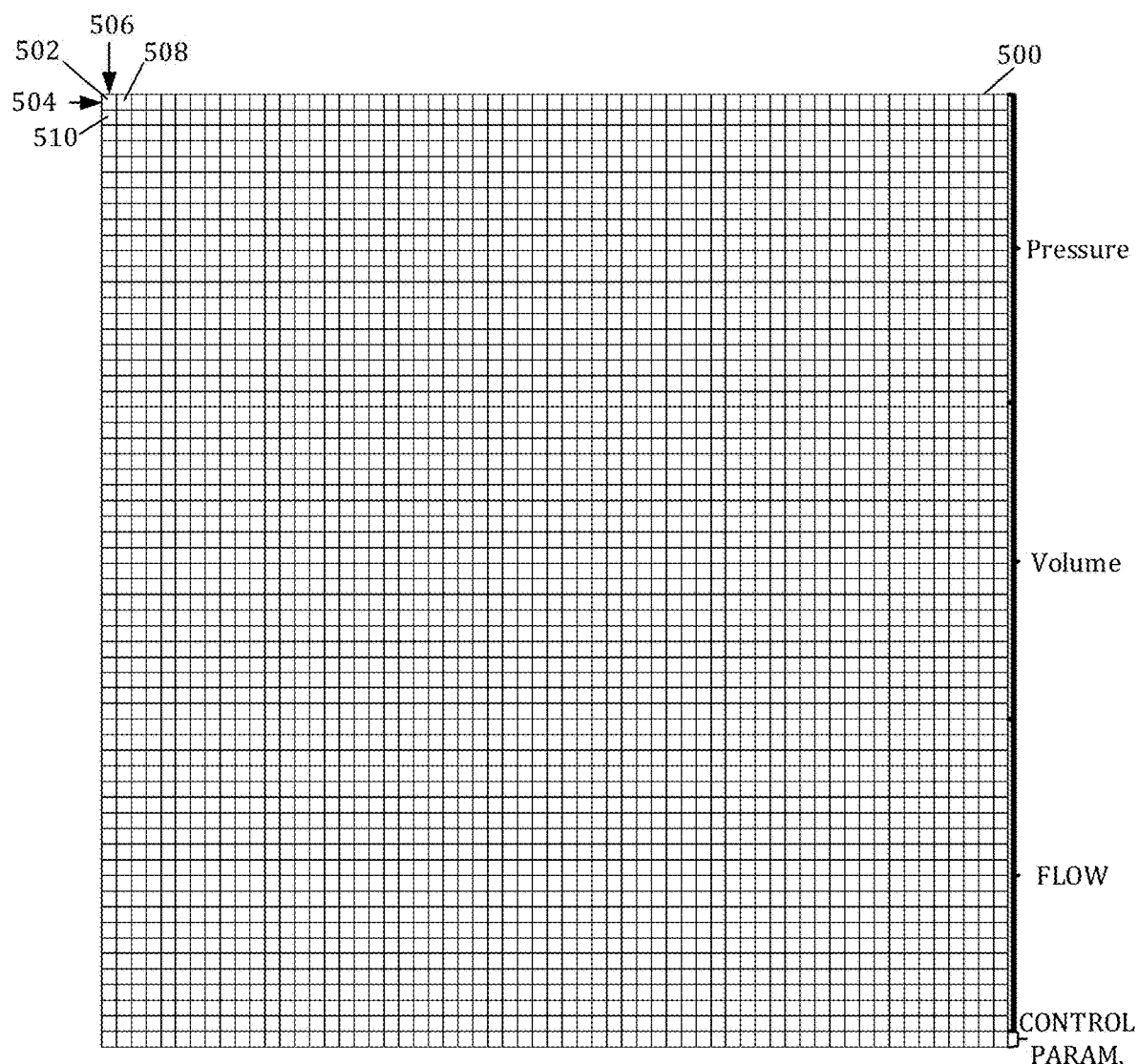
FIGS. 5A-B depict example human-indecipherable images.
Figure 5B:
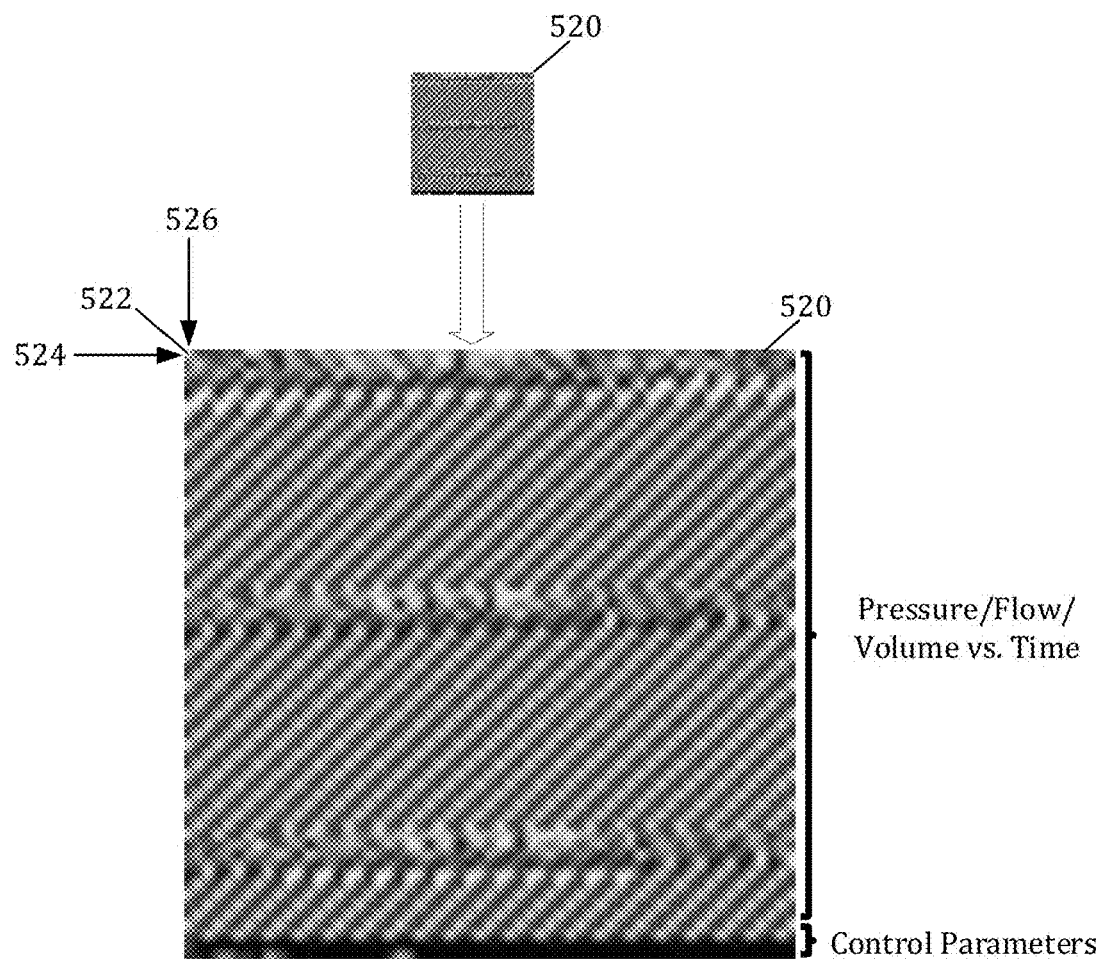

FIG. 5A depicts an example human-indecipherable image 500. The example human-indecipherable image 500 is 61×61 pixels. FIG. 5A depicts the example human-indecipherable image 500 in black and white for clarity purposes, but FIG. 5B depicts an example of an actual example human-indecipherable image 500 in color. In FIG. 5B, the human-indecipherable image 500 is shown in actual size towards the top of FIG. 5B, and an enlarged version is shown below for illustration and discussion. The pixels in the image 500 are arranged in pixel rows 504 and pixel columns 506. Each of the pixels is defined by color channels. In the example depicted, the human-indecipherable image 500 is an RGB image and each pixel 502 is defined by a red channel, a green channel, and a blue channel. The pixels may also be defined by a transparency channel, which is not utilized in the present example. Thus, each pixel may be defined by an array of three channel values, such as {Color1, Color2, Color3}. These three values define the color for an individual pixel. For the human-indecipherable image 500, the ventilatory data and the control parameters are stored as channel values for the pixels 502.

The location of each pixel may be defined by its row (i) and column (j), and the each pixel may be represented as $px_{(i,j)}$. For example, the pixel 502 in the upper-leftmost corner of the image 500 may be represented as $px_{(1,1)}$ because the pixel is in the first row and the first column. Similarly, a pixel 508 in the first row and second column may be represented as $px_{(1,2)}$, and a pixel 510 in the second row and the first column may be represented as $px_{(2,1)}$.

The location of the pixel defines the type of data that the pixel represents and the time point, if applicable, when the data was captured. For instance, the pixel $px_{(1,1)}$ 502 in the first row and first column of the human-indecipherable image 500 may correspond to ventilatory data, such as pressure, volume, or flow, recorded at a first time point in the time period (e.g., time=t1). The second pixel $px_{(1,2)}$ 508 in the first row 504 may represent ventilatory data recorded at a second time point in the time period (e.g., time=t2=t1+20 ms). The next pixels may continue to represent ventilatory data at subsequent time points. In examples where data is sampled for 1200 time points, the first 1200 pixels may represent pressure data at each of the 1200 time points. The first 1200 pixels may include multiple rows of pixels. For instance, the first 20 rows may represent pressure data. The next 1200 pixels may represent volume data at each of the 1200 time points, and the following 1200 pixels may then represent flow data at each of the 1200 time points. Thus, each or most pixels in the human-indecipherable image 500 represent data, unlike the human-decipherable image 400, which includes a substantial number of blank or black pixels. Accordingly, the human-indecipherable image 500 can be significantly smaller (e.g., fewer pixels) than the human-decipherable image 400 while still representing the same amount of data. As a result, the total size of the training data needed for training the ML model can be significantly smaller, which saves memory and processing resources. Utilization of smaller images may also result in faster processing and training times for the ML model so that classifications of clinical conditions may be provided more quickly.

Because many image formats support only integer values for channel values of the pixels 502, the ventilatory data, which is commonly provided in a floating decimal format, may need to be converted to an integer format for storage as one or more channel values. The conversion to an integer format may be accomplished through various techniques. One technique is to utilize a modulo operation. The modulo operation returns a remainder of a division in an integer format. The quotient of the division operation may be stored in a first channel and the remainder (from the modulo operation) may then be stored in a second channel. The sign of the data may then be stored in the third channel.

As an example, pressure data at a first time point may be represented as $p_0$. The channel values for the pixel representing $p_0$ may be as follows {Color1, Color2, Color3}={$p_0$/256, $p_0$ mod 256, sign}. In other words, the first channel value (Color1) is equal to integer value of the quotient resulting from $p_0$ divided by 256. The second channel value (Color2) is equal to the modulo (e.g., modulus/remainder) of the division operation of $p_0$ divided by 256. The third channel value (Color3) represents the sign of $p_0$. Thus, the three channel values represent the pressure data at the first time point, and the displayed color of the pixel 502 thus corresponds to the pressure data at the first time point. In the above operations, the divisor was set at 256, but other divisor values may be utilized. In addition, the pressure value (or respective ventilatory data value) may first be scaled up or down such that the quotient of the division operation is non-zero for at least some of the data points in the dataset. For instance, the pressure value may be multiplied by a scalar, such as 10 or 100, prior to the quotient or modulo operations being performed. Thus, the location of the pixel defines the type of ventilatory data and/or time point and the color of the pixel defines the value for the ventilatory data.

The above operations may be performed for each of the pressure data points in the data set to define pixels for each of the pressure data points. Similar operations may then be performed for the volume data and the flow data for defined pixels for each of the volume data points and the flow data points.

Another subset of pixels may correspond to the control parameters. For instance, the last row (or last few rows) of pixels may correspond to control parameters. One pixel may correspond to one control parameter. For example, 25 pixels may be used to represent 25 different control parameters. The position or location of the pixel in the human-indecipherable image 500 indicates which control parameter the pixel represents. For example, the pixel $px_{(61,1)}$ may represent inspiratory rate, and pixel $px_{(61,2)}$ may represent a maximum flow setting.

The value for the control parameter may be stored as channel values similarly to how the ventilatory data is stored as channel values, as discussed above. For example, a first channel value may represent the sign of the control parameter value, a second channel value may represent a quotient of the control parameter value from a division operation, and the third channel value may represent a modulus/remainder from the division operation. In some examples, depending on the value of a particular control parameter, the value may first be scaled up (or down) prior to the division operation. Thus, similar to the ventilatory data, the color of the respective pixel represents the value of the of the respective control parameter, and the location of the pixel represents which control parameter is being represented.

In an embodiment, a set of images 500 with the same defined layout or mapping for the pixels 502 is generated and used to train and utilize an ML model. For instance, the defined layout or mapping may define what data is to be stored in each pixel. As an example, the layout may set the first pixel as representing the pressure data recorded at the first time, the second pixel as representing the pressure data at the second time, and so forth. The number of pixels required to represent each type of ventilatory data is based on the time period for which the data was acquired and the rate at which the data was sampled during the time period. For instance, for three ventilatory parameters (e.g., pressure, flow, and volume) and 1200 time points, 3600 pixels may be utilized. The defined layout for the human-indecipherable image 500 may include an array or matrix of the types of ventilatory data or control parameters for which each pixel $px_{(i,j)}$ corresponds. Thus, every individual pixel in every generated human-indecipherable image 500 may represent the same type of data. Accordingly, there does not have to be any visual meaning to a human for the layout. The layout could potentially be arbitrary as long as the layout is consistent for training and use with the ML model that can identify patterns within the human-indecipherable image 500. In addition, similar to the human-decipherable images, by using a defined layout, the human-indecipherable images 500 can be platform or ventilator-agnostic. For instance, the human-indecipherable images 500 may be generated from ventilatory data generated from any type of ventilator.

A set of these human-indecipherable images 500 that correspond to known clinical conditions of patients may then be used to train an ML model. Then, new ventilatory data and control parameters are received from a patient being ventilated, and this data is converted to a human-indecipherable image 500 that has the same layout. The newly generated human-indecipherable image 500 may then be provided as input into the trained ML model, which can classify the new human-indecipherable image 500 as corresponding to a particular clinical condition.

Figure 6A:
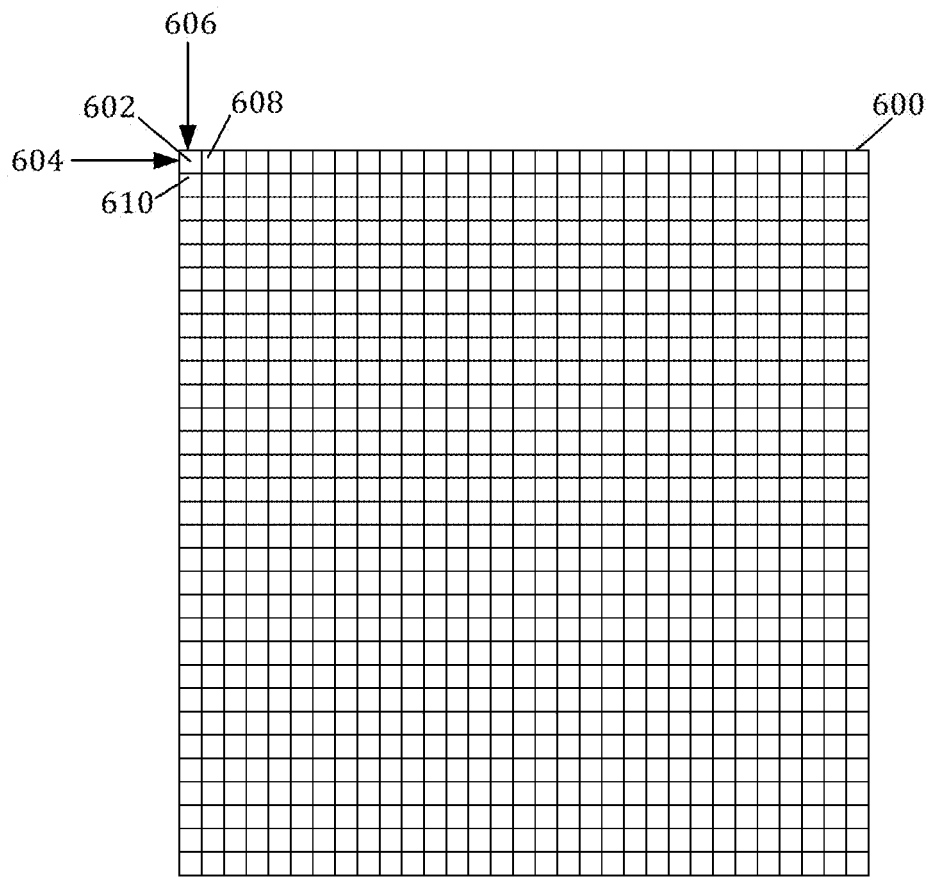
FIGS. 6A-B depict another type of example human-indecipherable images.
Figure 6B:
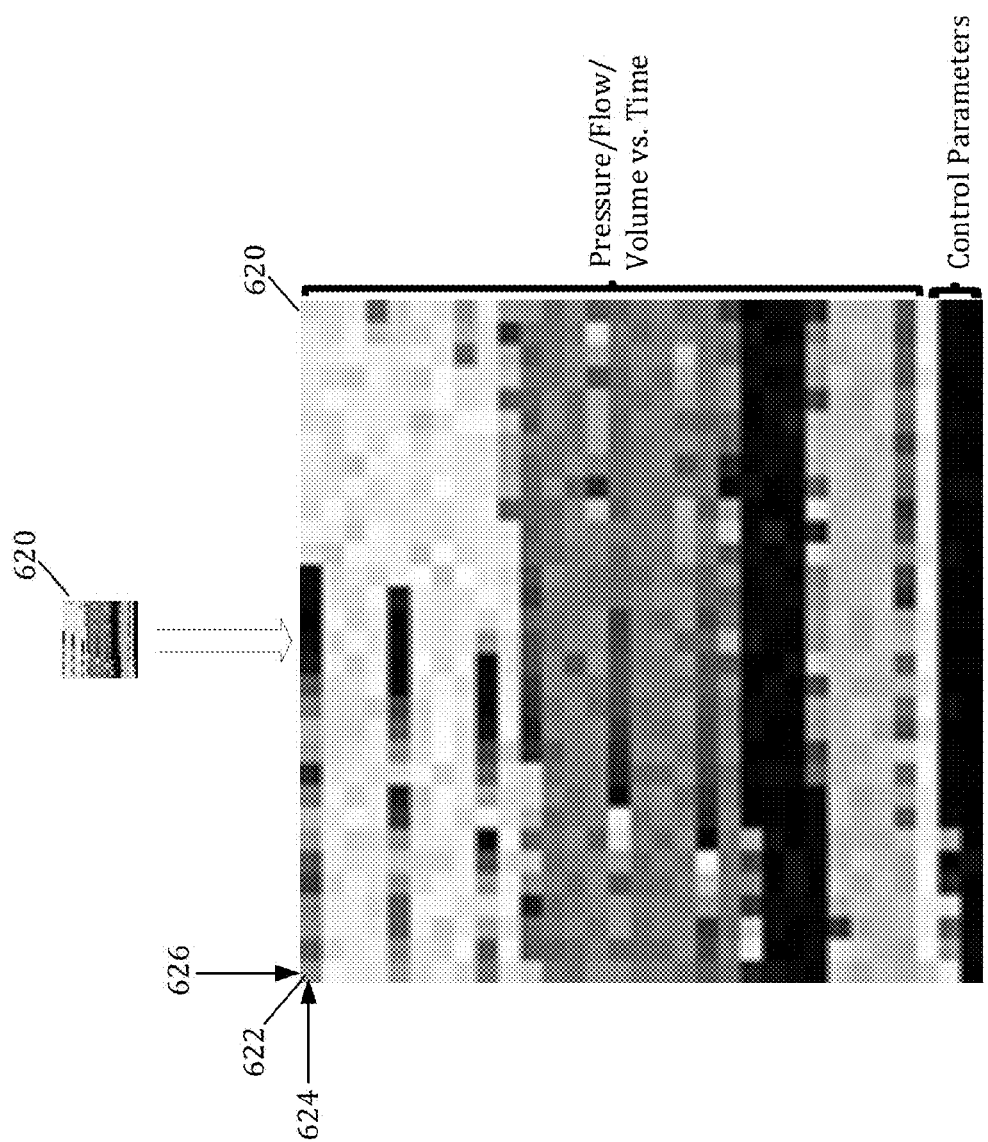

FIGS. 6A-6B depict another example human-indecipherable image 600. FIG. 6A depicts the example human-indecipherable image 600 in black and white for clarity purposes, but FIG. 6B depicts an example of an actual example human-indecipherable image 600 in color. In FIG. 6B, the human-indecipherable image 500 is shown in actual size towards the top of FIG. 6B, and an enlarged version is shown below for illustration and discussion. The human-indecipherable image 600 is similar to the human-indecipherable image 500 in FIGS. 5A-B, but the human-indecipherable image 600 has a different image format and/or layout that allows for data formatted as floating decimal points to be stored as channel values. One example of such an image format is a float4 image format. Because the image format allows for decimal values to be stored as channel values, additional information may be stored in each pixel via its channel values. In addition, the image format may provide for more usable channels that define each pixel 602. For example, image 600 may be saved using an RGBA format having a red channel, a blue channel, and an alpha channel. The image format may be based on the saveImageRGBA method of the Nvidia CUDA® platform. Due to these increased capacities for storing data as channel values, the human-indecipherable image 600 may be substantially smaller than the human-indecipherable image 500 in FIGS. 5A-B. For instance, the example human-indecipherable image 600 depicted in FIGS. 6A-6B is 31×31 pixels but stores as much information as the example human-indecipherable image 500 in FIGS. 5A-5B (which is 61×61 pixels). The pixels in image 600 may be addressed in a similar manner as the image 600 (e.g., by rows and columns). For instance, the location of each pixel may be defined by its row (i) and column (j), and the each pixel may be represented as $px_{(i,j)}$. The pixel 602 in the upper-leftmost corner of the image 600 may be represented as $px_{(1,1)}$ because the pixel is in the first row and the first column. Similarly, a pixel 608 in the first row and second column may be represented as $px_{(1,2)}$, and a pixel 610 in the second row and the first column may be represented as $px_{(2,1)}$.

For image 600, the data does not need to be converted into an integer format prior to being stored. Multiple data points are stored in the same pixel as different channel values. For example, the array of channel values for a pixel 602 may be {Color1, Color2, Color3, Color4}, where Color1 may correspond to red, Color2 may correspond to green, Color3 may correspond to blue, and Color4 may correspond to transparency. These four values together define the color and/or display for that individual pixel. Other color schemes are also possible. Each channel value may represent a different data point, such as ventilatory data at different time points. Accordingly, multiple different types of ventilatory data, or multiple time points of one type of ventilatory data, may be stored within a single pixel. Thus, in some examples, data from the three separate waveforms (pressure, volume, and flow) in the human-decipherable image 402 may be stored in a single pixel in the human indecipherable image 500. Similarly, the data stored in the four pixels of the human-indecipherable image 500 may be stored in a single pixel of the human-indecipherable image 600.

As an example, pressure data at first, second, third, and fourth time points may be represented by $p_0$, $p_1$, $p_2$, and $p_3$. Each of those pressure data points may be stored as a different channel value. For example, the array of channel values for the first pixel may be: {Color1, Color2, Color3, Color4}={$p_0$, $p_1$, $p_2$, $p_3$}. Thus, the first pixel 602 may represent the first four pressure data points. In contrast to the pixel 502 of human-indecipherable image 500, the pixel 602 of human-indecipherable image 600 is able to store four times as many data points. Thus, to represent 1200 data points, only 300 pixels may be used. As another example, different types of ventilatory data at a single time point may be stored in a pixel. For instance, the array of pixel values the array of channel values for the first pixel may be: {Color1, Color2, Color3}={$p_0$, $v_0$, $q_0$}, where $v_0$ is the volume at the first time point and $q_0$ is the flow at the first time point. In such an example, the transparency channel (Color4) may not be utilized, or the transparency channel may be utilized to store yet another type of ventilatory data.

Of note, in the example human-indecipherable image 600, separate channels may not be utilized to store the sign of the ventilatory data, unlike the human-indecipherable image 500 in FIG. 5. To adjust for lack of an explicit sign designation, the ventilatory data may be modified such that all the ventilatory data is a positive value. The modification may include shifting the ventilatory data by a defined amount. For example, the pressure data, volume data, and/or flow data may be increased by a constant amount that results in the respective data set being above zero (not having any negative values). The ventilatory data may also be normalized to a value, such as 1, prior to being stored as a channel value.

Storage of the control parameters may also be stored similarly in that values for multiple control parameters may be stored as different channel values of a single pixel. As an example, values for four different control parameters may be represented as $c_0$, $c_1$, $c_2$, and $c_3$. Each of those values may be stored as a different channel value. For example, the array of channel values for a pixel corresponding to control parameters may be: {Color1, Color2, Color3, Color4}={$c_0$, $c_1$, $c_2$, $c_3$}. Thus, a single pixel is able to store values for four different control parameters. Accordingly, in examples where 20 control parameters are utilized, five pixels may be utilized to represent the 20 control parameters at a particular time point.

The human-indecipherable image 600 may also have a defined layout or mapping for the pixels such that human-indecipherable images can be consistently generated and used to train and utilize an ML model. For instance, the defined layout or mapping may define what data is to be stored in each channel of each pixel. As an example, the layout may set the first 300 pixels to store pressure data in sequential order, the second 300 pixels to store volume data in sequential order, and the third 300 pixels to store flow data in sequential order. The number of pixels required to represent each type of ventilatory data is based on the time period for which the data was acquired and the rate at which the data was sampled during the time period. The defined layout may also set which pixels store which control parameter values. The format of the layout may be similar to the layout discussed above with respect to human-indecipherable image 500. For instance, the defined layout for the human-indecipherable image 600 may include an array or matrix of the types of ventilatory data or control parameters for which each pixel $px_{(i,j)}$ corresponds. As described above, new ventilatory data from a patient is converted into this format and passed to a trained ML model to classify clinical conditions of the patient.

Utilization of human-indecipherable images for ML models, such as human-indecipherable image 500 or human-indecipherable image 600, also proceeds against accepted wisdom in machine learning and computing. For instance, traditional wisdom may have suggested that using raw ventilatory data to train an ML model would have been more effective as the raw ventilatory data may comprise fewer bytes and overall smaller size. Certainly, the conversion of the ventilatory data into an image that has no visual meaning to human prior to training and using an ML model would have also been considered disadvantageous prior to the present disclosure because there would be no discernable patterns to a human.

Figure 7:
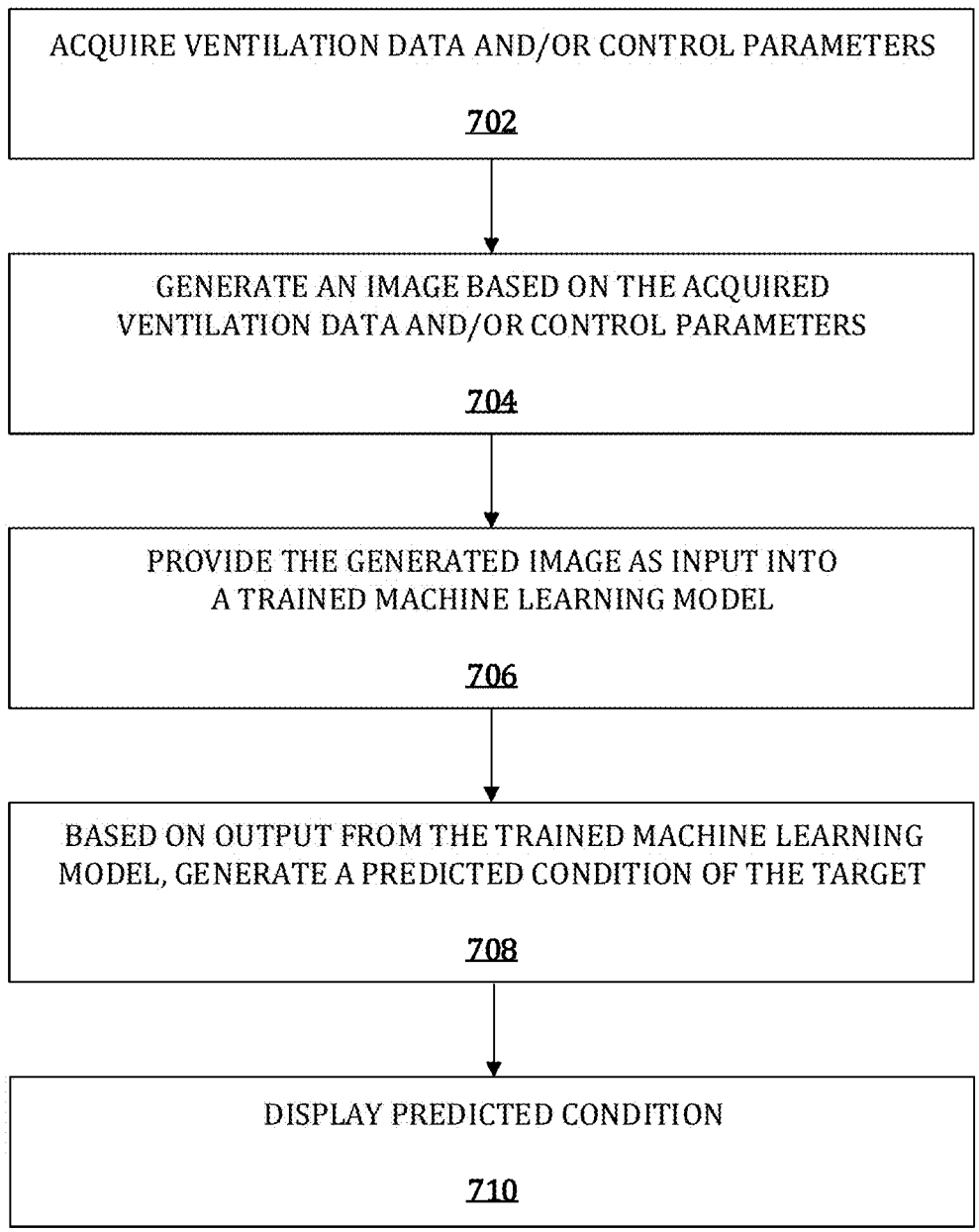
FIG. 7 depicts an example method for operating a ventilator.

FIG. 7 depicts an example method 700 for predicting a clinical condition of a ventilated patient. At operation 702, ventilatory data and/or control parameters during ventilation of a patient are acquired or received for a time period. The ventilatory data may include data such as pressure data, flow data, and/or volume data among other types of ventilatory data. In addition, additional patient data may also be received. The additional patient data may include data such as $CO_2$ measurements of the air exhaled from the patient, fractional oxygen measurements ($FiO_2$), patient's heart rate, patient's blood pressure, patient's blood oxygen saturation ($SpO_2$) The ventilatory data may be acquired by a ventilator, such as from sensors of the ventilator. For instance, a pressure sensor may measure pressure values at one or more locations of the ventilator or the patient circuit. The pressure data may include inspiratory pressure, expiratory pressure, wye pressure, and/or other pressure values. A flow sensor may also be used to measure flow values at one or more locations of the ventilator or the patient circuit. The flow data may include inspiratory flow, expiratory flow, net flow, or other flow values. The volume data may be calculated from the flow data (e.g., the integral of flow) rather than being measured. The ventilatory data may be sampled or recorded at a sampling rate, such as every 5 ms, 20 ms, or other frequency. The control parameters may be captured by recording the control parameters at the same or different sampling rate.

The ventilatory data and/or control parameters may also be acquired from the ventilator, such as by a remote computing device (e.g., a server). The ventilator may transmit the ventilatory data and/or control parameters to the server where the data is received by the server. The ventilator may continuously send the ventilatory data and/or control parameters as they are acquired or obtained. Alternatively, the ventilator may send the ventilatory data and/or control parameters in batches according to the time period. For instance, the data may be segregated into tranches or batches based on the time period. As an example, if the time period is 24 seconds and the sampling rate is once per 20 ms, then tranches of data for 1200 time points are generated. Accordingly, the ventilatory data and/or control parameters may be sent or stored as tranches for each time period.

At operation 704, an image is generated based on the ventilatory data and/or control parameters acquired in operation 702. The image may be generated for a tranche of the ventilatory data and/or control parameters. For instance, one image may be generated for all ventilatory data and/or all control parameters acquired over the time period. The image may also be generated based on additional patient data such as $CO_2$ measurements of the air exhaled from the patient, fractional oxygen measurements ($FiO_2$), patient's heart rate, patient's blood pressure, patient's blood oxygen saturation ($SpO_2$). The image may be generated by the ventilator itself or by the server in examples where the server acquired the ventilatory data and/or control parameters in operation 702.

The image generated in operation 702 may be a human-decipherable image, such as human-decipherable images 402A-C depicted in FIGS. 4A-4C, or a human-indecipherable image, such as human-indecipherable image 500 in FIGS. 5A-B or human-indecipherable image 600 in FIGS. 6A-6B. Generating the image may include converting the ventilatory data and/or control parameters into the image format according to a defined layout for the image. For instance, generating a human-decipherable image may include generating graphical representations of the ventilatory data, such as a pressure graphical representation, a volume graphical representation, and a flow graphical representation. Generating the human-decipherable image may also include generating a scale indicator and a control-parameters graphical representation. The graphical representations may then be incorporated into the image in the sections defined by the defined layout. For instance, graphical representations of the ventilatory data may be incorporated into a ventilatory data section, the scale indicator may be incorporated into a scale section, and the control-parameters graphical representation may be incorporated into a control parameters section. Graphical representations of the additional patient data may also be generated in the image. For example, where the additional patient data (e.g., heart rate) changes over time, the additional patient data may be plotted versus time similar to the ventilatory data. In other examples, an average or single value of the patient data may be utilized and presented as a bar in a bar graph or similar manner as how the graphical representations of the control parameters are generated.

Generating a human-indecipherable image may include storing the ventilatory data and/or control parameters as channel values for pixels in the human-indecipherable image, as discussed above with respect to FIGS. 5A-B and 6A-B. Where the image format of the human-indecipherable image requires integer values for the different channel values, the ventilatory data and/or control parameters may be converted to integer format through a division operation and a modulo operation. Accordingly, a first channel value for a pixel may represent a first portion of a data point value at time point and a second channel value for the pixel may represent a second portion of the data point value. A third channel of the pixel may represent a sign of the data point value. In other examples, where the human-indecipherable image has a format that supports floating decimal values, multiple data point values may be stored in the channel values of a pixel, as described above with respect to FIGS. 6A-B. In some examples, the multiple data point values may be modified and normalized such that there are no negative values. The ventilatory data and/or control parameters may be stored in the channel values of the pixels according to a defined layout for the pixels of the human-indecipherable image. In some examples, multiple images are generated for a single tranche of data at operation 704. For example, a human-decipherable image and one or more human-indecipherable images may be generated for the tranche of data.

In other examples, the image generated at operation 704 may be a screen capture from the ventilator display, such as the GUI displayed in FIG. 2. For instance, the ventilator display may include waveforms of ventilatory data versus time and indicators of control parameters. Thus, a screen capture of the ventilator display may provide an image that is representative of the ventilatory data and/or control parameters for a time period. The screen capture may be altered or cropped to remove some information from the screen, such as graphics, text, or other displayed components other than the waveforms and/or indicators of control parameters. As an example, in the example GUI 204 in FIG. 2, the screen capture may be cropped such that only certain sections remain, such as one or more of the plots 206-210 and/or one or more of the loops 212-214. In some examples, the patient data segment 216 and/or one of the first display section 218 and the second display section 220 may also be retained.

In some examples, the ventilator may enter a prediction mode where the ventilatory data waveforms and control parameters are displayed on the screen in a defined manner, such as according to a defined layout. The ventilator may enter into a prediction mode based on a manual input indicating a prediction mode. In other examples, the ventilator may enter into a prediction mode automatically according to a schedule or time frequency.

At operation 706, the image generated at operation 704 is provided to a trained machine learning (ML) model. The ML model is trained based on prior images that have the same defined layout as the image generated in operation 704. Training the ML model may include generating or acquiring a large data set of tranches of ventilatory data and/or control parameters for patients having known conditions. The ventilatory data and/or control parameters may be generated from actual patients or from simulated patients or lungs, such as the ASL 5000® breathing simulator by IngMar Medical. When utilizing a breathing simulator, a condition may be programmed into the breathing simulator, and tranches of ventilatory data and/or control parameters may be recorded when the breathing simulator is in a stable, non-alarming condition. Regardless of whether the tranches of training data are generated from a breathing simulator or ventilation of an actual patient, each of the tranches of data have a known associated condition. Thus, known tranches of data may be converted into images according to the defined layout and those images may be labeled according to the known conditions. The ML model may be trained by a supervised training method based on the labeled images. Additionally, the trained ML model may be stored on a server and/or a ventilator and be used to generate predictions of clinical conditions upon receipt of an image having the same defined layout as the images used to train the ML model.

The ML model may be neural network, such a convolutional neural network, a deep neural network, a recurrent neural network, or other type of neural network. Due to the benefits of image classification technologies, a convolution neural network may be preferable in some implementations. Other types of ML models may also be utilized, such as Hidden Markov Models (HMMs), support vector machines (SVMs), k-nearest neighbor, or the like. Because the ventilatory data and/or control parameters are converted into an image, the present technology is able to leverage the significant advances and investments in image recognition and classification technology through the use of specific ML models that have been the subject of significant advancement, development, and investment. Examples of such ML models include GoogleNet, AlexNet, VGG16, Inception, ResNet, SqueezeNet, among others. While many of these models have been focused in areas such as automated driving or the like, the present inventors have recognized the ability of these models to apply to ventilatory data once that data is integrated into an image, as discussed above.

At operation 708, a predicted condition of the patient is generated based on output from the trained ML model. The predicted condition may be generated by the ventilator or by a server depending on where the trained ML model is stored. The output from the ML model may include a classification of the image that was provided as the input. The classification itself may be the predicted condition. In other examples, the classification may be used to determine a condition of the patient. The condition of the patient may include conditions such as asthma, acute respiratory distress syndrome (ARDS), emphysema, chronic obstructive pulmonary disease (COPD), alveolar overdistention, attempts to breathe simultaneously while in a mandatory ventilation mode, readiness for weaning, etc. Classifications of ventilator conditions or conditions based on an interaction between the patient and the ventilator may also be classified. For instance, the identification of double or multiple breaths may be identified or classified by the ML model. Such an identification may indicate that a flow sensitivity setting is too low.

The output of the ML model may also include a confidence value for the classification provided. The confidence value may be a percentage of confidence that the classification is correct. Thus, the confidence value may also be associated with the prediction of the condition for the patient. In some examples, if the confidence value is a below a certain threshold (such as 90%), the classification of the condition may not be displayed, or the format of displaying the classification may be adjusted to highlight low confidence in the classification.

At operation 710, the predicted condition of the patient may be displayed or provided for display. For example, if a server generates the predicted condition in operation 708, the predicted condition may be transmitted to the ventilator for display on a display screen communicatively coupled to the ventilator. The ventilator may then display the predicted condition on the display screen. A display screen of the server may also or alternatively display the predicted condition. In examples where the ventilator generates the predicted condition, the ventilator may display the predicted condition on the display screen of the ventilator. Displaying the predicted condition may also include displaying the confidence score associated with the predicted condition. In other examples, the predicted condition may alternatively or additionally be displayed on another remote computing device. For example, the predicted condition may be displayed at a nurses' station or other central monitoring location within a hospital or medical facility.

Figure 8:
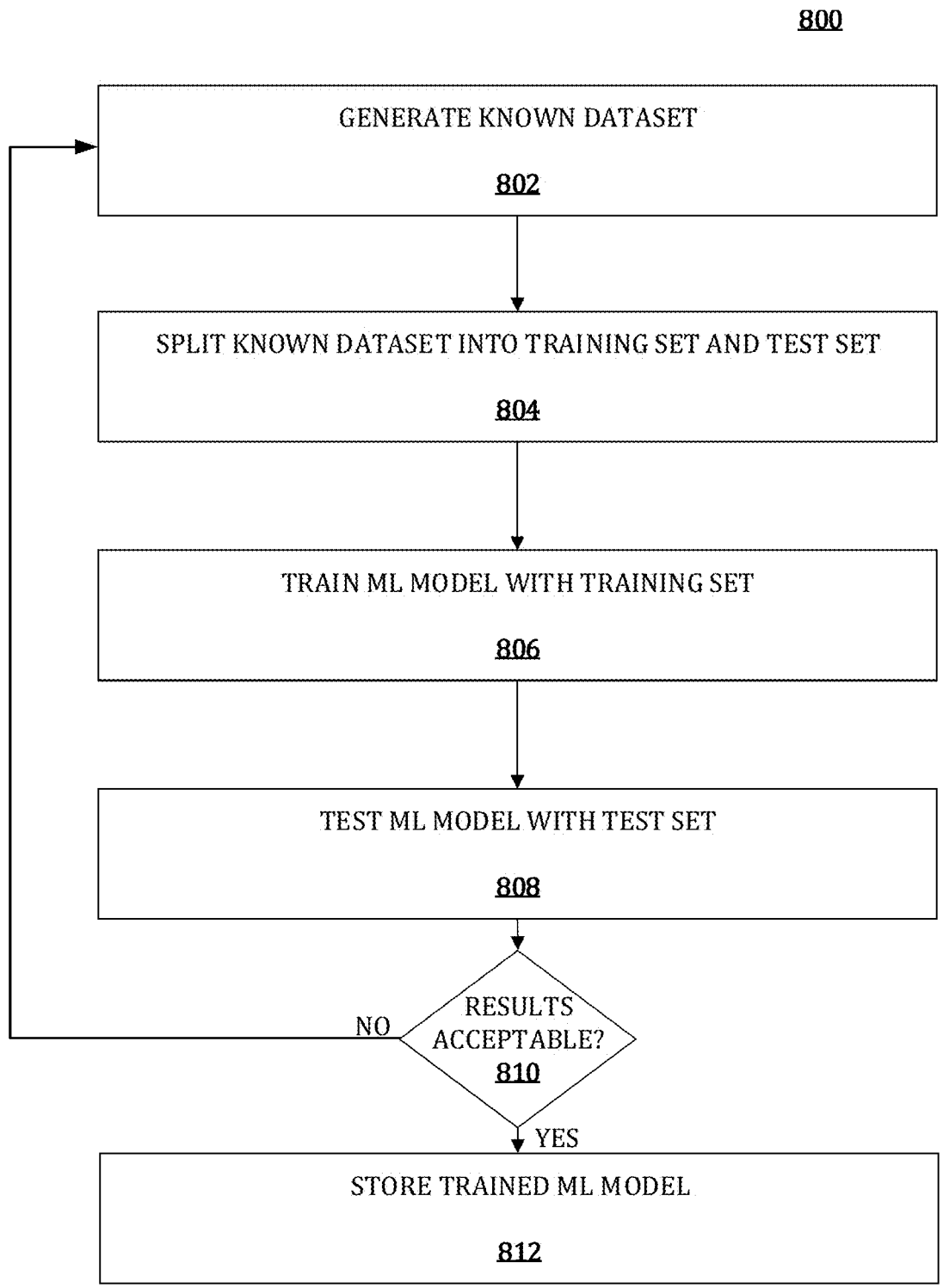
FIG. 8 depicts an example method for training a machine-learning model.

FIG. 8 depicts a method for training an ML model for use in classifying clinical conditions of a patient. At operation 802, a known dataset may be generated. The known dataset is dataset of set of tranches of ventilatory data and/or control parameters for patients having known conditions. The ventilatory data and/or control parameters may be generated from actual patients or from simulated patients or lungs, such as the ASL 5000® breathing simulator by IngMar Medical®. When utilizing a breathing simulator, a condition may be programmed into the breathing simulator, and tranches of ventilatory data and/or control parameters may be recorded when the breathing simulator is in a stable, non-alarming condition. Regardless of whether the tranches of training data are generated from a breathing simulator or ventilation of an actual patient, each of the tranches of data have a known associated condition. Thus, known tranches of data may be converted into images according to the defined layout and those images may be labeled according to the known conditions. The generated images may be human-indecipherable images or human-decipherable images depending on which type of image the ML model is to be used for. Each of the generated images may be stored with or correlated with their corresponding known condition.

At operation 804, the known dataset is split into a training set and a test set. For instance, 10% of the images in the known dataset may be used as a test set and the remaining 90% of the images may be used as the training set.

At operation 806, the ML model is trained with the training set. The training may be performed according to a supervised training algorithm. The images in the training data set are provided as the input and the corresponding conditions are provided as the known output such that the training of the ML model may be performed. Training the ML model may include modifying one or more variables or parameters based on the provided inputs (images) and the known outputs (corresponding conditions). As an example, the coefficients of a neural network may be adjusted to minimize a pre-defined cost function that evaluates the difference between the output of the neural network and known conditions.

Subsequent to training the ML model, the ML model is tested in operation 808. The ML model may be tested with the test data generated in operation 804 to determine the accuracy and performance of the ML model. At operation 810, based on the performance of the ML model in the testing operation 808, a determination is made as to whether the performance of the ML model is acceptable. The determination may be made based on differences between the output of the ML model and the test data set. If the performance is acceptable or within a determined tolerance, the trained ML network is stored at operation 812 for later use with live or real time images generated from ventilatory data of ventilated patients. If the performance is not acceptable or outside a predetermined tolerance, the method 800 flows back to operation 802 where additional data is generated to further train the ML model. The method 800 continues and repeats until the ML model generates acceptable results that are within the predetermined tolerance.

In addition to the predicted condition, recommended ventilation settings or modes may be provided and/or displayed. The recommended ventilation settings or modes may be based on the prior tranches of data that were utilized to train the ML model. The recommended ventilation settings or modes may also be based on best practices associated with the predicted condition. For example, for a patient predicted to have the clinical condition of ARDS, ventilation settings (e.g., increased PEEP or reduced tidal volume setting) and/or a particular ventilation mode may be recommended as medical literature and research indicates that the particular ventilation mode is well-suited for patients with an ARDS condition. As another example, if a double breath or multiple breath condition is detected, a recommended setting may include changing a flow sensitivity setting. A prompt to activate the recommended ventilation settings or mode may also be displayed and, upon a selection of the prompt, the ventilation settings or mode may be activated or applied. In other examples, the recommend ventilation settings may be automatically activated or applied upon the generation of the predicted condition.

In some examples, a confirm/reject prompt to a physician or medical professional may also be displayed with the predicted condition. The confirm/reject prompt allows the medical professional to either confirm or agree with the predicted condition or to reject or disagree with the predicted condition. The input to the confirm/reject prompt may then be used to positively or negatively reinforce the trained ML model.

Those skilled in the art will recognize that the methods and systems of the present disclosure may be implemented in many manners and as such are not to be limited by the foregoing aspects and examples. In other words, functional elements being performed by a single component, or multiple components, in various combinations of hardware and software or firmware, and individual functions, can be distributed among software applications at either the client or server level or both. In this regard, any number of the features of the different aspects described herein may be combined into single or multiple aspects, and alternate aspects having fewer than or more than all of the features herein described are possible.

Functionality may also be, in whole or in part, distributed among multiple components, in manners now known or to become known. Thus, a myriad of software/hardware/firmware combinations are possible in achieving the functions, features, interfaces, and preferences described herein. Moreover, the scope of the present disclosure covers conventionally known manners for carrying out the described features and functions and interfaces, and those variations and modifications that may be made to the hardware or software firmware components described herein as would be understood by those skilled in the art now and hereafter. In addition, some aspects of the present disclosure are described above with reference to block diagrams and/or operational illustrations of systems and methods according to aspects of this disclosure. The functions, operations, and/or acts noted in the blocks may occur out of the order that is shown in any respective flowchart. For example, two blocks shown in succession may in fact be executed or performed substantially concurrently or in reverse order, depending on the functionality and implementation involved.

Further, as used herein and in the claims, the phrase "at least one of element A, element B, or element C" is intended to convey any of: element A, element B, element C, elements A and B, elements A and C, elements B and C, and elements A, B, and C. In addition, one having skill in the art will understand the degree to which terms such as "about" or "substantially" convey in light of the measurement techniques utilized herein. To the extent such terms may not be clearly defined or understood by one having skill in the art, the term "about" shall mean plus or minus ten percent.

Numerous other changes may be made which will readily suggest themselves to those skilled in the art and which are encompassed in the spirit of the disclosure and as defined in the appended claims. While various aspects have been described for purposes of this disclosure, various changes and modifications may be made which are well within the scope of the disclosure. Numerous other changes may be made which will readily suggest themselves to those skilled in the art and which are encompassed in the spirit of the disclosure and as defined in the claims.

What is claimed is:

1. A computer-implemented method for recognition of conditions from ventilatory data, the method comprising:
   acquiring ventilatory data for ventilation of a patient during a time period;
   converting the ventilatory data to a human-indecipherable image having a plurality of pixels, wherein each of the pixels of the human-indecipherable image is defined by at least a first channel, and a first channel value of a first pixel represents at least a portion of a value for the ventilatory data;
   providing, as input into a trained machine learning model, the human-indecipherable image; and
   based on output from the trained machine learning model, generating a predicted condition of the patient.

2. The method of claim 1, wherein the ventilatory data includes at least one of pressure data, flow data, or volume data.

3. The method of claim 1, wherein the first pixel is further defined by a second channel value and a third channel value.

4. The method of claim 3, wherein the second channel value represents another portion of the value for the ventilatory data and the third channel value represents a sign for the ventilatory data.

5. The method of claim 3, wherein:
   the value for the ventilatory data represented by the first channel is a first value for ventilatory data at a first time point;
   the second channel value represents a second value for ventilatory data at a second time point; and
   the third channel value represents a third value for ventilatory data at a third time point.

6. The method of claim 5, wherein the first pixel is further defined a fourth channel value, and the fourth channel value represents a fourth value for ventilatory data a fourth time point.

7. The method of claim 1, further comprising acquiring control parameters during the time period, wherein the control parameters are also converted into the human-indecipherable image.

8. The method of claim 1, wherein the human-indecipherable image has a size of less than 4000 pixels.

9. The method of claim 1, wherein the human-indecipherable image has a size of less than 1600 pixels.

10. The method of claim 9, wherein the ventilatory data includes pressure data sampled for at least 1000 time points and flow data sampled for at least 1000 time points.

11. A computer-implemented method for recognition of conditions from ventilatory data, the method comprising:
    acquiring ventilatory data and control parameters for ventilation of a patient during a time period;
    converting the ventilatory data to a human-decipherable image having a defined layout including plurality of layout sections, including a first section for a graphical representation of ventilatory data and a second section for a graphical representation of control parameters;
    providing, as input into a trained machine learning model, the human-decipherable image, wherein the trained machine learning model was trained based on images having the defined layout; and
    based on output from the trained machine learning model, generating a predicted condition of the patient.

12. The computer-implemented method of claim 11, wherein the ventilatory data includes at least one of pressure data, flow data, or volume data.

13. The computer-implemented method of claim 12, wherein the first section includes a graphical representation of the pressure data in a first color and a graphical representation of flow in a second color.

14. The computer-implemented method of claim 13, wherein the graphical representation of the pressure data is a plot of pressure data versus time for the time period.

15. The computer-implemented method of claim 11, wherein the graphical representation of control parameters are represented as bars, wherein a height of each bar represents a value for a control parameter.

16. The computer-implemented method of claim 11, wherein the defined layout includes a third section for a scale of the ventilatory data.

17. A computer-implemented method for recognition of conditions from ventilation data, the method comprising:
- acquiring ventilation data for ventilation of a patient during a time period;
- generating an image based on the acquired ventilation data;
- providing, as input into a trained machine learning model, the generated image, wherein the trained machine learning model was trained based on images having a same type as the generated image; and
- based on output from the trained machine learning model, generating a predicted condition of the patient.

18. The computer-implemented method of claim 17, wherein the ventilation data includes at least one of pressure data, flow data, or volume data.

19. The computer-implemented method of claim 17, wherein the image is a human-decipherable image.

20. The computer-implemented method of claim 17, wherein the image is a human-indecipherable image.

* * * * *